(12) United States Patent
Schorr et al.

(10) Patent No.: US 7,763,061 B2
(45) Date of Patent: *Jul. 27, 2010

(54) THERMAL COVERINGS

(75) Inventors: Phillip A. Schorr, Atlanta, GA (US); Roger Bradshaw Quincy, III, Cumming, GA (US); Christopher D. Fenwick, Alpharetta, GA (US); Patricia A. Stern, Cumming, GA (US); Glynis Allicia Walton, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 734 days.

This patent is subject to a terminal disclaimer.

(21) Appl. No.: 11/021,483

(22) Filed: Dec. 23, 2004

(65) Prior Publication Data

US 2006/0142828 A1    Jun. 29, 2006

(51) Int. Cl.
*A61F 7/00* (2006.01)
(52) U.S. Cl. ................. 607/108; 607/109
(58) Field of Classification Search ......... 607/108–112, 607/114
See application file for complete search history.

(56) References Cited

U.S. PATENT DOCUMENTS

| | | | |
|---|---|---|---|
| 2,573,791 A | 11/1951 | Howells | |
| 3,261,347 A | 7/1966 | Sherman | |
| 3,266,973 A | 8/1966 | Crowley | |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,729,438 A * | 4/1973 | Plesich et al. | 524/806 |
| 3,736,303 A * | 5/1973 | Smith et al. | 526/240 |
| 3,794,497 A | 2/1974 | Pratt et al. | |
| 3,802,817 A | 4/1974 | Matsuki et al. | |
| 3,836,633 A | 9/1974 | Beschke | |

(Continued)

FOREIGN PATENT DOCUMENTS

EP    0251783 B1    1/1988

(Continued)

OTHER PUBLICATIONS

Abstract of Article—*Non-hydrothermal synthesis of copper-, zinc- and copper-zinc hydrosilicates*, T.M. Yurieva, G. N. Kustova, T. P. Minyukova, E. K. Poels, A. Bliek, M. P. Demeshkina, L. M. Plyasova, T. A. Krieger, V. I. Zaikovskii, Materials Research Innovations, vol. 5, No. 1, Jun. 2001, pp. 0003-0011.

(Continued)

*Primary Examiner*—Henry M Johnson, III
*Assistant Examiner*—Aaron Roane
(74) *Attorney, Agent, or Firm*—Dority & Manning P.A.

(57) ABSTRACT

A thermal covering that comprises a thermoregulatory substrate is provided. The thermoregulatory substrate contains an exothermic coating formed from an oxidizable metal. The exothermic coating is generally free of moisture prior to activation. Exposure of the exothermic coating to oxygen and moisture activates an exothermic reaction to generate heat, such heat being transferable to a patient or user through an outer surface defined by the thermal covering.

35 Claims, 8 Drawing Sheets

U.S. PATENT DOCUMENTS

| | | |
|---|---|---|
| 3,849,241 A | 11/1974 | Butin et al. |
| 3,901,236 A | 8/1975 | Assarsson et al. |
| 3,976,049 A | 8/1976 | Yamashita et al. |
| 4,076,663 A | 2/1978 | Masuda et al. |
| 4,100,324 A | 7/1978 | Anderson et al. |
| 4,106,477 A | 8/1978 | Feld |
| 4,285,343 A | 8/1981 | McNair |
| 4,286,082 A | 8/1981 | Tsubakimoto et al. |
| 4,297,233 A | 10/1981 | Gualandi |
| 4,323,534 A | 4/1982 | DesMarais |
| 4,340,563 A | 7/1982 | Appel et al. |
| 4,341,216 A | 7/1982 | Obenour |
| 4,423,118 A | 12/1983 | Corbett et al. |
| 4,469,746 A | 9/1984 | Weisman et al. |
| 4,516,564 A | 5/1985 | Koiso et al. |
| 4,517,308 A | 5/1985 | Ehlenz et al. |
| 4,525,410 A | 6/1985 | Hagiwara et al. |
| 4,608,047 A | 8/1986 | Mattingly |
| 4,663,220 A | 5/1987 | Wisneski et al. |
| 4,687,478 A | 8/1987 | Van Tilburg |
| 4,704,116 A | 11/1987 | Enloe |
| 4,734,324 A | 3/1988 | Hill |
| 4,747,841 A | 5/1988 | Kuratomi et al. |
| 4,756,299 A | 7/1988 | Podella |
| 4,758,239 A | 7/1988 | Yeo et al. |
| 4,775,585 A | 10/1988 | Hagiwara et al. |
| 4,798,603 A | 1/1989 | Meyer et al. |
| 4,834,738 A | 5/1989 | Kielpikowski et al. |
| 4,925,743 A | 5/1990 | Ikeda et al. |
| 4,950,264 A | 8/1990 | Osborn, III |
| 4,988,505 A | 1/1991 | Watanabe et al. |
| 5,009,653 A | 4/1991 | Osborn, III |
| 5,046,479 A | 9/1991 | Usui |
| 5,085,654 A | 2/1992 | Buell |
| 5,093,422 A | 3/1992 | Himes |
| 5,108,739 A | 4/1992 | Kurihara et al. |
| 5,122,418 A | 6/1992 | Nakane et al. |
| 5,176,668 A | 1/1993 | Bernardin |
| 5,176,672 A | 1/1993 | Bruemmer et al. |
| 5,178,139 A | 1/1993 | Angelillo et al. |
| 5,183,656 A | 2/1993 | Uesaka et al. |
| 5,190,563 A | 3/1993 | Herron et al. |
| 5,192,606 A | 3/1993 | Proxmire et al. |
| 5,197,959 A | 3/1993 | Buell |
| 5,213,881 A | 5/1993 | Timmons et al. |
| 5,252,657 A * | 10/1993 | Frankel et al. ............... 524/460 |
| 5,267,992 A | 12/1993 | Van Tilburg |
| 5,272,236 A | 12/1993 | Lai et al. |
| 5,277,180 A | 1/1994 | Angelillo et al. |
| 5,278,272 A | 1/1994 | Lai et al. |
| 5,284,703 A | 2/1994 | Everhart et al. |
| 5,304,599 A | 4/1994 | Himes |
| 5,308,346 A | 5/1994 | Sneller et al. |
| 5,316,837 A | 5/1994 | Cohen |
| 5,332,613 A | 7/1994 | Taylor et al. |
| 5,342,342 A | 8/1994 | Kitaoka |
| 5,350,624 A | 9/1994 | Georger et al. |
| 5,382,400 A | 1/1995 | Pike et al. |
| 5,397,667 A | 3/1995 | Law et al. |
| 5,407,741 A | 4/1995 | Ota |
| 5,418,945 A | 5/1995 | Carter et al. |
| 5,420,090 A | 5/1995 | Spencer et al. |
| 5,425,975 A | 6/1995 | Koiso et al. |
| 5,454,363 A | 10/1995 | Sata |
| 5,480,636 A | 1/1996 | Maruo et al. |
| 5,486,166 A | 1/1996 | Bishop et al. |
| 5,486,356 A | 1/1996 | Yim |
| 5,487,938 A | 1/1996 | Spencer et al. |
| 5,490,846 A | 2/1996 | Ellis et al. |
| 5,509,914 A | 4/1996 | Osborn, III |
| 5,509,915 A | 4/1996 | Hanson et al. |
| 5,539,056 A | 7/1996 | Yang et al. |
| 5,562,994 A | 10/1996 | Abba et al. |
| 5,569,234 A | 10/1996 | Buell et al. |
| RE35,427 E | 1/1997 | Poettgen |
| 5,596,052 A | 1/1997 | Resconi et al. |
| 5,599,585 A | 2/1997 | Cohen |
| 5,628,737 A | 5/1997 | Dobrin et al. |
| 5,634,916 A | 6/1997 | Lavon et al. |
| 5,649,916 A | 7/1997 | DiPalma et al. |
| 5,656,355 A | 8/1997 | Cohen |
| 5,662,624 A | 9/1997 | Sundström et al. |
| 5,672,306 A | 9/1997 | Sprang et al. |
| 5,693,385 A | 12/1997 | Parks |
| 5,702,375 A | 12/1997 | Angelillo et al. |
| 5,702,378 A | 12/1997 | Widlund et al. |
| 5,716,349 A | 2/1998 | Taylor et al. |
| 5,770,528 A | 6/1998 | Mumick |
| 5,817,300 A | 10/1998 | Cook et al. |
| 5,834,114 A | 11/1998 | Economy et al. |
| 5,836,932 A | 11/1998 | Buell et al. |
| 5,843,057 A | 12/1998 | McCormack |
| 5,855,999 A | 1/1999 | McCormack |
| 5,879,378 A * | 3/1999 | Usui ........................ 607/96 |
| 5,885,599 A | 3/1999 | Peterson et al. |
| 5,906,879 A | 5/1999 | Huntoon et al. |
| 5,925,072 A | 7/1999 | Cramer et al. |
| 5,932,497 A | 8/1999 | Morman et al. |
| 5,948,398 A | 9/1999 | Hanamoto et al. |
| 5,975,074 A | 11/1999 | Koiso et al. |
| 5,984,995 A | 11/1999 | White |
| 5,997,981 A | 12/1999 | McCormack et al. |
| 6,002,064 A | 12/1999 | Kobylivker et al. |
| 6,015,764 A | 1/2000 | McCormack et al. |
| 6,019,782 A | 2/2000 | Davis et al. |
| 6,037,281 A | 3/2000 | Mathis et al. |
| 6,096,299 A | 8/2000 | Guarracino et al. |
| 6,099,556 A | 8/2000 | Usui |
| 6,110,158 A | 8/2000 | Kielpikowski |
| 6,111,163 A | 8/2000 | McCormack et al. |
| 6,114,024 A | 9/2000 | Forte |
| 6,127,294 A | 10/2000 | Koiso et al. |
| 6,149,934 A | 11/2000 | Krzysik et al. |
| 6,153,209 A | 11/2000 | Vega et al. |
| 6,197,045 B1 | 3/2001 | Carson |
| 6,198,018 B1 | 3/2001 | Curro |
| 6,203,810 B1 | 3/2001 | Alemany et al. |
| 6,245,401 B1 | 6/2001 | Ying et al. |
| 6,264,681 B1 | 7/2001 | Usui |
| 6,265,631 B1 | 7/2001 | Angelillo et al. |
| 6,277,346 B1 | 8/2001 | Murasawa et al. |
| 6,277,772 B1 | 8/2001 | Gancet et al. |
| 6,299,867 B1 | 10/2001 | Aoyagi et al. |
| 6,358,499 B2 | 3/2002 | Hall-Puzio et al. |
| 6,358,537 B1 | 3/2002 | Hoshino et al. |
| 6,436,128 B1 | 8/2002 | Usui |
| 6,461,457 B1 | 10/2002 | Taylor et al. |
| 6,465,709 B1 | 10/2002 | Sun et al. |
| 6,486,227 B2 | 11/2002 | Nohr et al. |
| 6,517,906 B1 | 2/2003 | Economy et al. |
| 6,573,212 B2 | 6/2003 | McCrae et al. |
| 6,576,810 B1 | 6/2003 | Underhill et al. |
| 6,639,004 B2 | 10/2003 | Falat et al. |
| 6,639,119 B2 | 10/2003 | Roe et al. |
| 6,648,909 B2 | 11/2003 | Helming |
| 6,653,356 B2 | 11/2003 | Sherman |
| 6,663,611 B2 | 12/2003 | Blaney et al. |
| 6,680,289 B1 | 1/2004 | Woo et al. |
| 6,740,406 B2 | 5/2004 | Hu et al. |
| 6,770,064 B1 | 8/2004 | Ruscher |
| 6,791,004 B2 | 9/2004 | Sprengard-Eichel et al. |
| 6,794,024 B1 | 9/2004 | Walton et al. |
| 6,915,798 B2 * | 7/2005 | Minami ............... 126/263.02 |
| 7,081,211 B2 | 7/2006 | Li et al. |

| | | | |
|---|---|---|---|
| 7,338,516 B2 * | 3/2008 | Quincy et al. ............... 607/96 |
| 2001/0023338 A1 | 9/2001 | Guarracino et al. |
| 2002/0066542 A1 | 6/2002 | Jakob et al. |
| 2002/0121624 A1 | 9/2002 | Usui |
| 2002/0142937 A1 | 10/2002 | Carter et al. |
| 2002/0161420 A1 | 10/2002 | Usui |
| 2003/0050211 A1 | 3/2003 | Hage et al. |
| 2003/0120253 A1 | 6/2003 | Wentzel et al. |
| 2003/0203009 A1 | 10/2003 | MacDonald |
| 2004/0063603 A1 | 4/2004 | Dave et al. |
| 2004/0120904 A1 | 6/2004 | Lye et al. |
| 2004/0120921 A1 | 6/2004 | Quincy, III et al. |
| 2004/0121681 A1 | 6/2004 | Lindsay et al. |
| 2004/0121688 A1 | 6/2004 | Edens et al. |
| 2004/0122387 A1 | 6/2004 | Long et al. |
| 2004/0166248 A1 | 8/2004 | Hu et al. |
| 2004/0178384 A1 | 9/2004 | Usui |
| 2005/0028806 A1 | 2/2005 | Kumamoto et al. |
| 2005/0084464 A1 | 4/2005 | McGrath et al. |

FOREIGN PATENT DOCUMENTS

| | | | |
|---|---|---|---|
| EP | 0370600 A1 | 5/1990 |
| EP | 0427475 A | 5/1991 |
| EP | 0749295 B1 | 12/1996 |
| EP | 0786240 A1 | 7/1997 |
| EP | 0856302 A1 | 8/1998 |
| EP | 1034800 A1 | 9/2000 |
| EP | 1112702 A1 | 7/2001 |
| EP | 1162172 A1 | 12/2001 |
| EP | 1214878 A1 | 6/2002 |
| EP | 1315526 B1 | 6/2003 |
| EP | 1566156 A1 | 8/2005 |
| GB | 2297490 A | 8/1996 |
| WO | WO 9111977 A1 | 8/1991 |
| WO | WO 9112030 A1 | 8/1991 |
| WO | WO 9725076 A1 | 7/1997 |
| WO | WO 9820915 A1 | 5/1998 |
| WO | WO 9826808 A2 | 6/1998 |
| WO | WO 9826808 A3 | 6/1998 |
| WO | WO 9829079 A1 | 7/1998 |
| WO | WO 9900093 A1 | 1/1999 |
| WO | WO 9912734 A1 | 3/1999 |
| WO | WO 0029036 A2 | 5/2000 |
| WO | WO 0029036 A3 | 5/2000 |
| WO | WO 0059555 A1 | 10/2000 |
| WO | WO 0103619 A1 | 1/2001 |
| WO | WO 0103624 A2 | 1/2001 |
| WO | WO 0103624 A3 | 1/2001 |
| WO | WO 0249559 A2 | 6/2002 |
| WO | WO 02055115 A1 | 7/2002 |
| WO | WO 03025067 A1 | 3/2003 |
| WO | WO 03092885 A1 | 11/2003 |
| WO | WO 04000986 A1 | 12/2003 |
| WO | WO 2004108589 A2 | 12/2004 |
| WO | WO 2004108589 A3 | 12/2004 |

OTHER PUBLICATIONS

Abstract of Japanese Patent No. JP01262868, Oct. 19, 1989.
Abstract of Japanese Patent No. JP02142561, May 31, 1990.
Abstract of Japanese Patent No. JP02157039, Jun. 15, 1990.
Abstract of Japanese Patent No. JP03152894, Jun. 28, 1991.
Abstract of Japanese Patent No. JP03221142, Sep. 30, 1991.
Abstract of Japanese Patent No. JP07256025, Oct. 9, 1995.
Abstract of Japanese Patent No. JP08112303, May 7, 1996.
Abstract of Japanese Patent No. JP08173471, Jul. 9, 1996.
Abstract of Japanese Patent No. JP09143872, Jun. 3, 1997.
Article—*Adsorption Of Gases In Multimolecular Layers*, Stephen Brunauer, P. H. Emmett, and Edward Teller, The Journal of the American Chemical Society, vol. 60, Feb. 1938, pp. 309-319.
Article—*Immobilization of $(n-Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Alessandro Mazzacani, and Giovanni Sartori, Journal of Catalysis, vol. 209, 2002, pp. 210-216.
Article—*Mesoporous Sieves with Unified Hybrid Inorganic/Organic Frameworks*, Brian J. Melde, Brian T. Holland, Christopher F. Blanford, and Andreas Stein, Chem. Mater., vol. 11, 1999, pp. 3302-3308.
U.S. Appl. No. 11/022,299, filed Dec. 23, 2004, Bradshaw et al., Method For Applying An Exothermic Coating To A Substrate.
U.S. Appl. No. 11/021,546, filed Dec. 23, 2004, Roger B. Quincy, III, Absorbent Articles That Provide Warmth.
U.S. Appl. No. 10/723,761, filed Nov. 26, 2003, Quincy, III, et al., Odor Control In Personal Care Products.
Abstract of Japanese Patent No. JP04255767, Sep. 10, 1992.
Abstract of Japanese Patent No. JP05098185, Apr. 20, 1993.
Search Report and Written Opinion for PCT/US2005/034360, Feb. 8, 2006.
Abstract of Japanese Patent No. JP2004143232, May 20, 2004.
Written Opinion and Search Report for PCT/US2005/034363, May 4, 2006.
Written Opinion and Search Report for PCT/US2005/035499, May 8, 2006.

* cited by examiner

THERMAL COVERINGS

BACKGROUND OF THE INVENTION

In many emergency situations, it is critical for a patient to receive prompt and proper attention to his/her injuries in order to avoid exacerbating those injuries that may have already occurred. Often, the first rescuers to arrive on the scene are emergency medical staff who are responsible for preparing the patient for transportation to the nearest medical facility where the individual's injuries are to be treated. Depending upon the particular circumstances surrounding the patient's injuries and the location of an accident scene, these rescuers may be emergency medical squads who are employed with either a fire department, a local hospital, a law enforcement agency, rescue patrols, etc. One of the many concerns of certified rescue workers during their preliminary treatment of a patient is to provide, to the extent possible, the most comfortable surroundings for the individual. This may place the patient at ease and may be vital to the success or failure of initial medical treatment, particularly in instances where weather conditions are severe or where the patient is in shock. For instance, rescues that take place in cold or wet weather conditions, such as those often encountered by ski patrols, require that the patient be adequately insulated from the cold to avoid further reduction in body temperature, while rescues occurring in windy or rainy climates require that the patient be covered with a material repellant to these elements. Therefore, it is vital that the emergency rescue personnel be adequately equipped so that they may quickly and properly adapt to the specific situation at hand.

The patient may remain at the medical facility and require continued thermal protection to provide heat to his/her body. In addition, the patient may be required to undergo a surgical procedure. It is well known that a patient under general anesthesia undergoes several physiological changes that inhibit the body's normal thermoregulatory capabilities. General anesthesia depresses the function of thermoregulating centers in the hypothalamus, thus resulting in the body's diminished ability to self-regulate body temperature. Infusion of intravenous fluid may also contribute to cooling body temperature during surgery because such intravenous fluids absorb heat from the body when they are at a temperature below body temperature. Inspiration of dry anesthesia gases during surgery may also contribute to body temperature cooling during surgery because the dry gas both absorbs heat from the body and because of the cooling action created when water from the body is absorbed by the dry gas. Moreover, during surgery the body cavity may be exposed, which increases the effective surface area of the body and also cools body parts that are normally not exposed to the environment. The incidence of hypothermia occurring after surgery has been estimated to be as great as 60% to 90%. To prevent hypothermia from occurring in many situations, including rescue, emergency surgery, and/or many elective surgeries, it is desired to provide active heating to the patient.

Many conventional devices exist for providing heat. For example, U.S. Pat. No. 6,436,128 to Usui describes an exothermic composition that contains an exothermic substance, a water-absorptive polymer and/or tackifier, a carbon component and/or metal halide, and water. An excessive amount of water is used in the composition to suppress a premature oxidation reaction with air. Once formulated, the exothermic composition of Usui is laminated and sealed in a thin pouch. The pouch absorbs water from the composition so that, when the seal is broken, the exothermic reaction may proceed upon exposure to air and moisture. Despite having some benefits, Usui is simply too complex and difficult to control for most applications.

As such, a need currently exists for an improved thermal covering that is simple, effective, and relatively inexpensive.

SUMMARY OF THE INVENTION

In accordance with one embodiment of the present invention, a thermal covering is disclosed that comprises an exothermic coating formed from an oxidizable metal. The exothermic coating is generally free of moisture prior to activation. Exposure of the exothermic coating to oxygen and moisture activates an exothermic reaction to generate heat, such heat being transferable to a patient or user through an outer surface defined by the thermal covering.

In accordance with another embodiment of the present invention, a thermal covering is disclosed that comprises a substrate containing an exothermic coating, the exothermic coating being formed from an oxidizable metal powder. The exothermic coating is generally free of moisture prior to activation. Exposure of the exothermic coating to oxygen and moisture activates an exothermic reaction to generate heat. The thermal covering further comprises an absorbent layer for absorbing and retaining moisture and a breathable layer for regulating the amount of moisture and oxygen contacting the substrate.

In accordance with still another embodiment of the present invention, a thermal covering is disclosed that comprises first and second substrates, each of which contain an exothermic coating that is formed from an oxidizable metal powder. The exothermic coating is generally free of moisture prior to activation. Exposure of the exothermic coating to oxygen and moisture activates an exothermic reaction to generate heat. The thermal covering further comprises first and second breathable layers for regulating the amount of moisture and oxygen contacting the exothermic coating, and an absorbent layer for absorbing and retaining moisture. The absorbent layer is positioned between the first and second substrates, the first substrate is positioned between the absorbent layer and first breathable layer, and the second substrate is positioned between the absorbent layer and second breathable layer.

In accordance with still another embodiment of the present invention, a method for forming a thermal covering is disclosed. The method comprises providing a substrate containing an exothermic coating formed from an oxidizable metal; supplying moisture to an absorbent layer; positioning the absorbent layer relative to the substrate so that moisture is capable of transferring from the absorbent layer to the exothermic coating; and sealing the absorbent layer and substrate within an enclosure to inhibit the passage of oxygen to the exothermic coating. For example, to warm a patient, the enclosure may be removed to expose the exothermic coating to oxygen and generate heat, such heat causing one or more surfaces of the thermal covering to have an elevated temperature. The thermal covering having the elevated temperature may then be contacted with the patient.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Definitions

Figure 1:
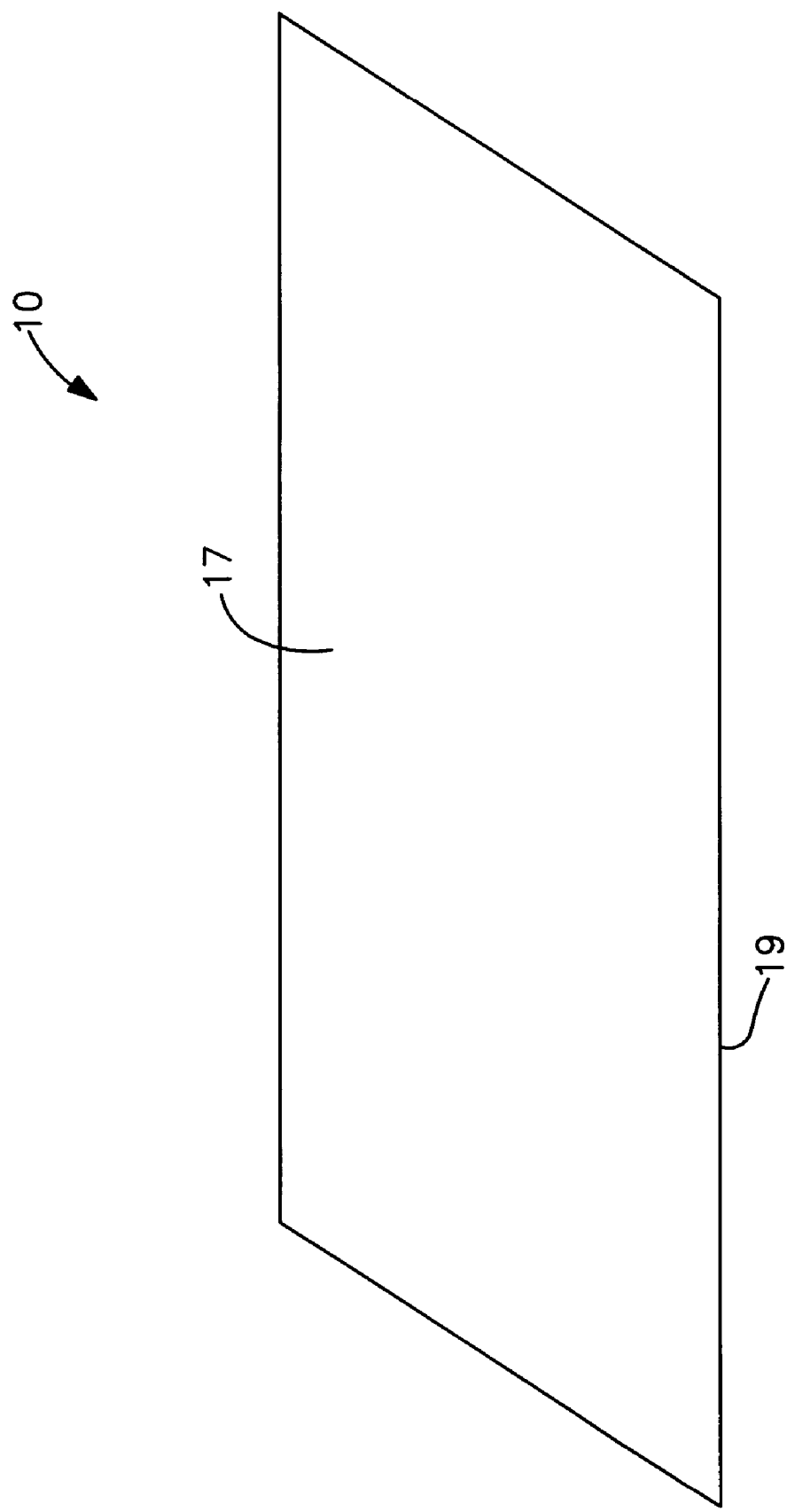
FIG. 1 illustrates a perspective view of one embodiment of a thermal covering of the present invention.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbonded fibers are generally not tacky when they are deposited onto a collecting surface. Spunbonded fibers may sometimes have diameters less than about 40 microns, and are often between about 5 to about 20 microns.

As used herein, the term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, et al.; which are incorporated herein in their entirety by reference thereto for all purposes.

As used herein, the "water vapor transmission rate" (WVTR) generally refers to the rate at which water vapor permeates through a material as measured in units of grams per meter squared per 24 hours ($g/m^2/24$ hrs). The test used to determine the WVTR of a material may vary based on the nature of the material. For instance, in some embodiments, WVTR may be determined in general accordance with ASTM Standard E-96E-80. This test may be particularly well suited for materials thought to have a WVTR of up to about 3,000 $g/m^2/24$ hrs. Another technique for measuring WVTR involves the use of a PERMATRAN-W 100K water vapor permeation analysis system, which is commercially available from Modern Controls, Inc. of Minneapolis, Minn. Such a system may be particularly well suited for materials thought to have a WVTR of greater than about 3,000 $g/m^2/24$ hrs. However, as is well known in the art, other systems and techniques for measuring WVTR may also be utilized.

As used herein, the term "breathable" means pervious to water vapor and gases, but impermeable to liquid water. For instance, "breathable barriers" and "breathable films" allow water vapor to pass therethrough, but are substantially impervious to liquid water. The "breathability" of a material is measured in terms of water vapor transmission rate (WVTR), with higher values representing a more vapor-pervious material and lower values representing a less vapor-pervious material. Breathable materials may, for example, have a water vapor transmission rate (WVTR) of at least about 100 grams per square meter per 24 hours ($g/m^2/24$ hours), in some embodiments from about 500 to about 20,000 $g/m^2/24$ hours, and in some embodiments, from about 1,000 to about 15,000 $g/m^2/24$ hours.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to a thermal covering that contains an exothermic coating capable of generating heat upon activation. The exothermic coating may be formed from a variety of different components, including oxidizable metals, carbon components, binders, electrolytic salts, and so forth. The oxidizable metal is capable of undergoing an exothermic reaction in the presence of oxygen and moisture to generate heat. Examples of such metals include, but are not limited to, iron, zinc, aluminum, magnesium, and so forth. Although not required, the metal may be initially provided in powder form to facilitate handling and to reduce costs. Various methods for removing impurities from a crude metal (e.g. iron) to form a powder include, for example, wet processing techniques, such as solvent extraction, ion exchange, and electrolytic refining for separation of metallic elements; hydrogen gas ($H_2$) processing for removal of gaseous elements, such as oxygen and nitrogen; floating zone melting refining method. Using such techniques, the metal purity may be at least about 95%, in some embodiments at least about 97%, and in some embodiments, at least about 99%. The particle size of the metal powder may also be less than about 500 micrometers, in some embodiments less than about 100 micrometers, and in some embodiments, less than about 50 micrometers. The use of such small particles may enhance the contact surface of the metal with air, thereby improving the likelihood and efficiency of the desired exothermal reaction. The concentration of the metal powder employed may generally vary depending on the nature of the metal powder, and the desired extent of the exothermal/oxidation reaction. In most embodiments, the metal powder is present in the exothermic coating in an amount from about 40 wt. % to about 95 wt. %, in some embodiments from about 50 wt. % to about 90 wt. %, and in some embodiments, from about 60 wt. % to about 80 wt. %.

In addition to an oxidizable metal, a carbon component may also be utilized in the exothermic coating of the present invention. Without intending to be limited in theory, it is believed that such a carbon component promotes the oxidation reaction of the metal and acts as a catalyst for generating heat. The carbon component may be activated carbon, carbon black, graphite, and so forth. When utilized, activated carbon may be formed from sawdust, wood, charcoal, peat, lignite, bituminous coal, coconut shells, etc. Some suitable forms of activated carbon and techniques for formation thereof are described in U.S. Pat. Nos. 5,693,385 to Parks; 5,834,114 to Economy, et al.; 6,517,906 to Economy, et al.; 6,573,212 to McCrae, et al., as well as U.S. Patent Application Publication Nos. 2002/0141961 to Falat, et al. and 2004/0166248 to Hu, et al., all of which are incorporated herein in their entirety by reference thereto for all purposes.

The exothermic coating may also employ a binder for enhancing the durability of the exothermic coating when applied to a substrate. The binder may also serve as an adhesive for bonding one substrate to another substrate. Generally speaking, any of a variety of binders may be used in the exothermic coating of the present invention. Suitable binders may include, for instance, those that become insoluble in water upon crosslinking. Crosslinking may be achieved in a variety of ways, including by reaction of the binder with a polyfunctional crosslinking agent. Examples of such crosslinking agents include, but are not limited to, dimethylol urea melamine-formaldehyde, urea-formaldehyde, polyamide epichlorohydrin, etc.

In some embodiments, a polymer latex may be employed as the binder. The polymer suitable for use in the lattices typically has a glass transition temperature of about 30° C. or less so that the flexibility of the resulting substrate is not substantially restricted. Moreover, the polymer also typically has a glass transition temperature of about −25° C. or more to minimize the tackiness of the polymer latex. For instance, in some embodiments, the polymer has a glass transition temperature from about −150° C. to about 15° C., and in some embodiments, from about −10° C. to about 0° C. For instance, some suitable polymer lattices that may be utilized in the present invention may be based on polymers such as, but are not limited to, styrene-butadiene copolymers, polyvinyl acetate homopolymers, vinyl-acetate ethylene copolymers, vinyl-acetate acrylic copolymers, ethylene-vinyl chloride copolymers, ethylene-vinyl chloride-vinyl acetate terpolymers, acrylic polyvinyl chloride polymers, acrylic polymers, nitrile polymers, and any other suitable anionic polymer latex polymers known in the art. The charge of the polymer lattices described above may be readily varied, as is well known in the art, by utilizing a stabilizing agent having the desired charge during preparation of the polymer latex. Specific techniques for a carbon/polymer latex system are described in more detail in U.S. Pat. No. 6,573,212 to McCrae, et al. Commercially available activated carbon/polymer latex systems that may be used in the present invention include Nuchar® PMA, DPX-8433-68A, and DPX-8433-68B, all of which are available from MeadWestvaco Corp of Stamford, Conn.

Although polymer lattices may be effectively used as binders in the present invention, such compounds sometimes result in a reduction in drapability and an increase in residual odor. Thus, the present inventors have discovered that water-soluble organic polymers may also be employed as binders to alleviate such concerns. For example, one class of water-soluble organic polymers found to be suitable in the present invention is polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

Suitable cellulosic ethers may include, for instance, those available from Akzo Nobel of Stamford, Conn. under the name "BERMOCOLL." Still other suitable cellulosic ethers are those available from Shin-Etsu Chemical Co., Ltd. of Tokyo, Japan under the name "METOLOSE", including METOLOSE Type SM (methycellulose), METOLOSE Type SH (hydroxypropylmethyl cellulose), and METOLOSE Type SE (hydroxyethylmethyl cellulose). One particular example of a suitable nonionic cellulosic ether is ethyl hydroxyethyl cellulose having a degree of ethyl substitution (DS) of 0.8 to 1.3 and a molar substitution (MS) of hydroxyethyl of 1.9 to 2.9. The degree of ethyl substitution represents the average number of hydroxyl groups present on each anhydroglucose unit that have been reacted, which may vary between 0 and 3. The molar substitution represents the average number of hydroxethyl groups that have reacted with each anhydroglucose unit. One such cellulosic ether is BERMOCOLL E 230FQ, which is an ethyl hydroxyethyl cellulose commercially available from Akzo Nobel. Other suitable cellulosic ethers are also available from Hercules, Inc. of Wilmington, Del. under the name "CULMINAL."

The concentration of the carbon component and/or binder in the exothermic coating may generally vary based on the desired properties of the substrate. For example, the amount of the carbon component is generally tailored to facilitate the oxidation/exothermic reaction without adversely affecting other properties of the substrate. Typically, the carbon component is present in the exothermic coating in an amount about 0.01 wt. % to about 20 wt. %, in some embodiments from about 0.1 wt. % to about 15 wt. %, and in some embodiments, from about 1 wt. % to about 12 wt. %. In addition, although relatively high binder concentrations may provide better physical properties for the exothermic coating, they may likewise have an adverse effect on other properties, such as the absorptive capacity of the substrate to which it is applied. Conversely, relatively low binder concentrations may reduce the ability of the exothermic coating to remain affixed on the substrate. Thus, in most embodiments, the binder is present in the exothermic coating in an amount from about 0.01 wt. % to about 20 wt. %, in some embodiments from about 0.1 wt. % to about 10 wt. %, and in some embodiments, from about 0.5 wt. % to about 5 wt. %.

Still other components may also be employed in the exothermic coating of the present invention. For example, as is well known in the art, an electrolytic salt may be employed to react with and remove any passivating oxide layer(s) that might otherwise prevent the metal from oxidizing. Suitable electrolytic salts may include, but are not limited to, alkali halides or sulfates, such as sodium chloride, potassium chloride, etc.; alkaline halides or sulfates, such as calcium chloride, magnesium chloride, etc., and so forth. When employed, the electrolytic salt is typically present in the exothermic coating in an amount from about 0.01 wt. % to about 10 wt. %, in some embodiments from about 0.1 wt. % to about 8 wt. %, and in some embodiments, from about 1 wt. % to about 6 wt. %.

In addition, particles may also be employed in the exothermic coating that act as moisture retainers. That is, prior to the oxidation/exothermic reaction, these particles may retain moisture. However, after the reaction has proceeded to a certain extent and the moisture concentration is reduced, the particles may release the moisture to allow the reaction to continue. Besides acting as a moisture retainer, the particles may also provide other benefits to the exothermic coating of the present invention. For example, the particles may alter the black color normally associated with the carbon component and/or metal powder. When utilized, the size of the moisture-retaining particles may be less than about 500 micrometers, in some embodiments less than about 100 micrometers, and in some embodiments, less than about 50 micrometers. Likewise, the particles may be porous. Without intending to be limited by theory, it is believed that porous particles may provide a passage for air and/or water vapors to better contact the metal powder. For example, the particles may have pores/channels with a mean diameter of greater than about 5 angstroms, in some embodiments greater than about 20 angstroms, and in some embodiments, greater than about 50 angstroms. The surface area of such particles may also be greater than about 15 square meters per gram, in some embodiments greater than about 25 square meters per gram, and in some embodiments, greater than about 50 square meters per gram. Surface area may be determined by the physical gas adsorption (B.E.T.) method of Bruanauer, Emmet, and Teller, *Journal of American Chemical Society*, Vol. 60, 1938, p. 309, with nitrogen as the adsorption gas.

In one particular embodiment, porous carbonate particles (e.g., calcium carbonate) are used to retain moisture and also to alter the black color normally associated with activated carbon and/or metal powder. Such a color change may be more aesthetically pleasing to a user, particularly when the coating is employed on substrates designed for consumer/personal use. Suitable white calcium carbonate particles are commercially available from Omya, Inc. of Proctor, Vt. Still other suitable particles that may retain moisture include, but are not limited to, silicates, such as calcium silicate, alumina silicates (e.g., mica powder, clay, etc.), magnesium silicates (e.g., talc), quartzite, calcium silicate fluorite, vermiculite, etc.; alumina; silica; and so forth. The concentration of the particles may generally vary depending on the nature of the particles, and the desired extent of exothermic reaction and color alteration. For instance, the particles may be present in the exothermic coating in an amount from about 0.01 wt. % to about 30 wt. %, in some embodiments from about 0.1 wt. % to about 20 wt. %, and in some embodiments, from about 1 wt. % to about 15 wt. %.

In addition to the above-mentioned components, other components, such as surfactants, pH adjusters, dyes/pigments/inks, etc., may also be included in the exothermic coating of the present invention. Although not required, such additional components typically constitute less than about 5 wt. %, in some embodiments less than about 2 wt. %, and in some embodiments, from about 0.001 wt. % to about 1 wt. % of the exothermic coating.

As stated above, it is generally desired that the exothermic coating be coated onto a substrate in accordance with the present invention. The substrate may perform other functions of the thermal covering, such as described below, or it may simply be used as a physical carrier for the exothermic coating. Generally speaking, any type of substrate may be applied with the exothermic coating in accordance with the present invention. For instance, nonwoven fabrics, woven fabrics, knit fabrics, paper web, film, foams, etc., may be applied with the exothermic coating. When utilized, the nonwoven fabrics may include, but are not limited to, spunbonded webs (apertured or non-apertured), meltblown webs, bonded carded webs, air-laid webs, coform webs, hydraulically entangled webs, and so forth. Typically, the polymers used to form the substrate have a softening or melting temperature that is higher than the temperature needed to evaporate moisture. One or more components of such polymers may have, for instance, a softening temperature of from about 100° C. to about 400° C., in some embodiments from about 110° C. to about 300° C., and in some embodiments, from about 120° C. to about 250° C. Examples of such polymers may include, but are not limited to, synthetic polymers (e.g., polyethylene, polypropylene, polyethylene terephthalate, nylon 6, nylon 66, KEVLAR™, syndiotactic polystyrene, liquid crystalline polyesters, etc.); cellulosic polymers (softwood pulp, hardwood pulp, thermomechanical pulp, etc.); combinations thereof; and so forth.

To apply the exothermic coating of the present invention to a substrate, the components may initially be dissolved or dispersed in a solvent. For example, one or more of the above-mentioned components may be mixed with a solvent, either sequentially or simultaneously, to form a coating formulation that may be easily applied to a substrate. Any solvent capable of dispersing or dissolving the components is suitable, for example water; alcohols such as ethanol or methanol; dimethylformamide; dimethyl sulfoxide; hydrocarbons such as pentane, butane, heptane, hexane, toluene and xylene; ethers such as diethyl ether and tetrahydrofuran; ketones and aldehydes such as acetone and methyl ethyl ketone; acids such as acetic acid and formic acid; and halogenated solvents such as dichloromethane and carbon tetrachloride; as well as mixtures thereof. In one particular embodiment, for example, water is used as the solvent so that an aqueous coating formulation is formed. The concentration of the solvent is generally high enough to inhibit oxidization of the metal prior to use. Specifically, when present in a high enough concentration, the solvent may act as a barrier to prevent air from prematurely contacting the oxidizable metal. If the amount of solvent is too small, however, the exothermic reaction may occur prematurely. Likewise, if the amount of solvent is too large, the amount of metal deposited on the substrate might be too low to provide the desired exothermal effect. Although the actual concentration of solvent (e.g., water) employed will generally depend on the type of oxidizable metal and the substrate on which it is applied, it is nonetheless typically present in an amount from about 10 wt. % to about 80 wt. %, in some embodiments from about 20 wt. % to about 70 wt. %, and in some embodiments, from about 25 wt. % to about 60 wt. % of the coating formulation.

The amount of the other components added to the coating formulation may vary depending on the amount of heat desired, the wet pick-up of the application method utilized, etc. For example, the amount of the oxidizable metal (in powder form) within the coating formulation generally ranges from about 20 wt. % to about 80 wt. %, in some embodiments from about 30 wt. % to about 70 wt. %, and in some embodiments, from about 35 wt. % to about 60 wt. %. In addition, the carbon component may constitute from about 0.1 wt. % to about 20 wt. %, in some embodiments from about 0.1 wt. % to about 15 wt. %, and in some embodiments, from about 0.2 wt. % to about 10 wt. %. of the coating formulation. Binders may constitute from about 0.01 wt. % to about 20 wt. %, in some embodiments from about 0.1 wt. % to about 15 wt. %, and in some embodiments, from about 1 wt. % to about 10 wt. % of the coating formulation. Electrolytic salts may constitute from about 0.01 wt. % to about 10 wt. %, in some embodiments from about 0.1 wt. % to about 8 wt. %, and in some embodiments from about 1 wt. % to about 5 wt. %. of the coating formulation. Further, moisture-retaining particles may constitute from about 2 wt. % to about 30 wt. %, in some embodiments from about 3 wt. % to about 25 wt. %, and in some embodiments from about 4 wt. % to about 10 wt. %. of the coating formulation. Other components, such as surfactants, pH adjusters, etc., may also constitute from about 0.001 wt. % to about 0.5 wt. %, in some embodiments from about 0.01 wt. % to about 0.1 wt. %, and in some embodiments from about 0.02 wt. % to about 0.08 wt. % of the coating formulation.

The solids content and/or viscosity of the coating formulation may be varied to achieve the desired amount of heat generation. For example, the coating formulation may have a solids content of from about 30% to about 80%, in some embodiments from about 40% to about 70%, and in some embodiments, from about 50% to about 60%. By varying the solids content of the coating formulation, the presence of the metal powder and other components in the exothermic coating may be controlled. For example, to form an exothermic coating with a higher level of metal powder, the coating formulation may be provided with a relatively high solids content so that a greater percentage of the metal powder is incorporated into the exothermic coating during the application process. In addition, the viscosity of the coating formulation may also vary depending on the coating method and/or type of binder employed. For instance, lower viscosities may be employed for saturation coating techniques (e.g., dip-coating), while higher viscosities may be employed for drop-coating techniques. Generally, the viscosity is less than about $2 \times 10^6$ centipoise, in some embodiments less than about $2 \times 10^5$ centipoise, in some embodiments less than about $2 \times 10^4$ centipoise, and in some embodiments, less than about $2 \times 10^3$ centipoise, such as measured with a Brookfield DV-1 viscometer with an LV spindle. If desired, thickeners or other viscosity modifiers may be employed in the coating formulation to increase or decrease viscosity.

The coating formulation may be applied to a substrate using any conventional technique, such as bar, roll, knife, curtain, print (e.g., rotogravure), spray, slot-die, drop-coating, or dip-coating techniques. The materials that form the substrate (e.g., fibers) may be coated before and/or after incorporation into the substrate. The coating may be applied to one or both surfaces of the substrate. For example, the exothermic coating may be present on a surface of the substrate that is opposite to that facing the wearer or user to avoid the possibility of burning. In addition, the coating formulation may cover an entire surface of the substrate, or may only cover a portion of the surface. When applying the exothermic coating to multiple surfaces, each surface may be coated sequentially or simultaneously.

Regardless of the manner in which the coating is applied, the resulting coated substrate is heated to a certain temperature to remove the solvent and any moisture from the coating. For example, the coated substrate may be heated to a temperature of at least about 100° C., in some embodiments at least about 110° C., and in some embodiments, at least about 120° C. In this manner, the resulting dried exothermic coating is anhydrous, i.e., generally free of water. By minimizing the amount of moisture, the exothermic coating is less likely to react prematurely and generate heat. That is, the oxidizable metal does not generally react with oxygen unless some minimum amount of water is present. Thus, the exothermic coating may remain inactive until placed in the vicinity of moisture (e.g., next to an absorbent layer) during use. It should be understood, however, that relatively small amounts of water may still be present in the exothermic coating without causing a substantial exothermic reaction. In some embodiments, for example, the exothermic coating contains water in an amount less than about 0.5% by weight, in some embodiments less than about 0.1% by weight, and in some embodiments, less than about 0.01% by weight.

The solids add-on level of the exothermic coating may also be varied as desired. The "solids add-on level" is determined by subtracting the weight of the untreated substrate from the weight of the treated substrate (after drying), dividing this calculated weight by the weight of the untreated substrate, and then multiplying by 100%. Lower add-on levels may optimize certain properties (e.g., absorbency), while higher add-on levels may optimize heat generation. In some embodiments, for example, the add-on level is from about 100% to about 5000%, in some embodiments from about 200% to about 2400%, and in some embodiments, from about 400% to about 1200%. The thickness of the exothermic coating may also vary. For example, the thickness may range from about 0.01 millimeters to about 5 millimeters, in some embodiments, from about 0.01 millimeters to about 3 millimeters, and in some embodiments, from about 0.1 millimeters to about 2 millimeters. In some cases, a relatively thin coating may be employed (e.g., from about 0.01 millimeters to about 0.5 millimeters). Such a thin coating may enhance the flexibility of the substrate, while still providing uniform heating.

To maintain absorbency, porosity, flexibility, and/or some other characteristic of the substrate, it may sometimes be desired to apply the exothermic coating so as to cover less than 100%, in some embodiments from about 10% to about 80%, and in some embodiments, from about 20% to about 60% of the area of one or more surfaces of the substrate. For instance, in one particular embodiment, the exothermic coating is applied to the substrate in a preselected pattern (e.g., reticular pattern, diamond-shaped grid, dots, and so forth). Although not required, such a patterned exothermic coating may provide sufficient warming to the substrate without covering a substantial portion of the surface area of the substrate. This may be desired to optimize flexibility, absorbency, or other characteristics of the substrate. It should be understood, however, that the coating may also be applied uniformly to one or more surfaces of the substrate. In addition, a patterned exothermic coating may also provide different functionality to each zone. For example, in one embodiment, the substrate is treated with two or more patterns of coated regions that may or may not overlap. The regions may be on the same or different surfaces of the substrate. In one embodiment, one region of a substrate is coated with a first exothermic coating, while another region is coated with a second exothermic coating. If desired, one region may provide a different amount of heat than another region.

Besides having functional benefits, the coated substrate may also have various aesthetic benefits as well. For example, although containing activated carbon, the coated substrate may be made without the black color commonly associated with activated carbon. In one embodiment, white or light-colored particles (e.g., calcium carbonate, titanium dioxide, etc.) are employed in the exothermic coating so that the resulting substrate has a grayish or bluish color. In addition, various pigments, dyes, and/or inks may be employed to alter the color of the exothermic coating. The substrate may also be applied with patterned regions of the exothermic coating to form a substrate having differently colored regions.

Figure 2:
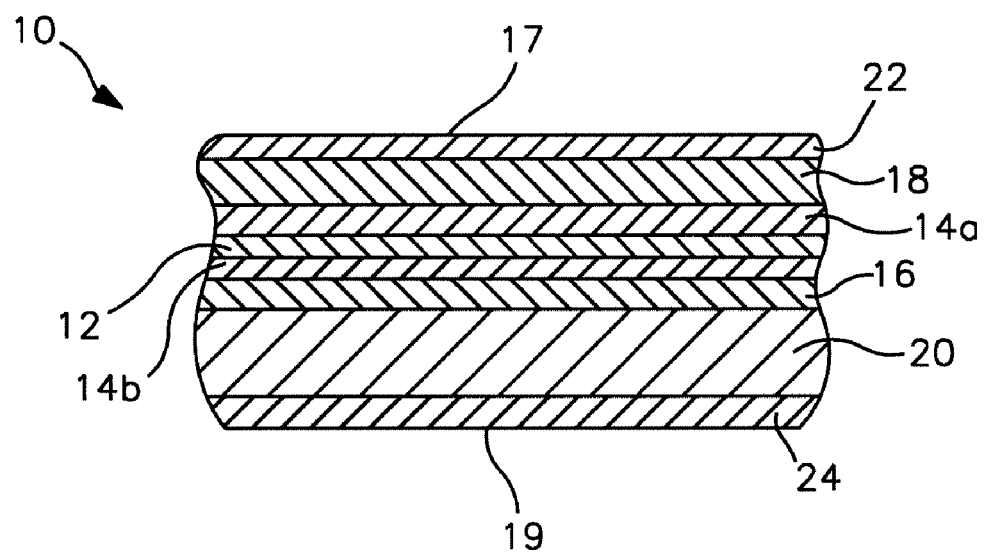
FIG. 2 illustrates a cross-sectional view of the thermal covering of FIG. 1.

In accordance with the present invention, the exothermic coating is incorporated into a thermal covering to provide warmth to a user. In this regard, various embodiments of thermal coverings that may be used in the present invention will now be described in greater detail. It should be understood, however, that the description below is merely exemplary, and that other thermal covering configurations are also contemplated by the present inventors. Referring to FIGS. 1-2, for example, one embodiment of a thermal covering 10 that may be formed in accordance with the present invention is shown. As shown, the thermal covering 10 defines two outer surfaces 17 and 19, and is in the form of a substantially flat, conformable, and foldable material. The overall size and shape of the covering 10 are not critical. For example, the covering 10 may have a shape that is generally triangular, square, rectangular, pentagonal, hexagonal, circular, elliptical, etc.

Regardless, of the overall shape and/or size of the thermal covering 10, it generally includes an integral thermoregulatory substrate 12 that is coated with the exothermic coating in the manner described above. Activation of the exothermic coating is accomplished by contacting the coating with reactants for the oxidizable metal, i.e., moisture and oxygen. However, if the amount of moisture that contacts the exothermic coating is too great, the moisture may act as a barrier to prevent air from prematurely contacting the oxidizable metal. Likewise, if the amount of moisture is too small, the exothermic coating may not fully react to provide an optimal amount of heat. Thus, it is typically desired to control the amount of moisture and air that contacts the exothermic coating during the activation step. For example, in some embodiments, breathable layers 14a and 14b may be included within the thermal covering 10 that are impermeable to liquids, but permeable to gases. This permits the flow of air for activating the exothermic reaction, but prevents an excessive amount of liquids from contacting the thermoregulatory substrate 12, which could either suppress the reaction or result in an excessive amount of heat that overly warms or burns the user. It should be understood that, although shown herein as having two breathable layers, any number of breathable layers (if any) may be employed in the present invention.

The breathable layers 14a and 14b may generally be formed from a variety of materials as is well known in the art. For example, the breathable layers 14a and 14b may contain a breathable film, such as a microporous or monolithic film. The film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

If desired, the breathable film may also contain an elastomeric polymer, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety (e.g., poly(vinyl arene)) and wherein B is an elastomeric polymer midblock, such as a conjugated diene or a lower alkene polymer (e.g., polystyrene-poly(ethylene-butylene)-polystyrene block copolymers). Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer. Commercially available A-B-A' and A-B-A-B copolymers include several different formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S or styrene-poly(ethylene-propylene)-styrene elastomeric copolymer available from Kuraray Company, Ltd. of Okayama, Japan, under the trade name SEPTON®.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. Nos. 5,539,056 to Yang, et al. and 5,596,052 to Resconi, et al., which are incorporated herein in their entirety by reference thereto for all purposes.

If desired, blends of two or more polymers may also be utilized to form the breathable film. For example, the film may be formed from a blend of a high performance elastomer and a lower performance elastomer. A high performance elastomer is generally an elastomer having a low level of hysteresis, such as less than about 75%, and in some embodiments, less than about 60%. Likewise, a low performance elastomer is generally an elastomer having a high level of hysteresis, such as greater than about 75%. The hysteresis value may be determined by first elongating a sample to an ultimate elongation of 50% and then allowing the sample to retract to an amount where the amount of resistance is zero. Particularly suitable high performance elastomers may include styrenic-based block copolymers, such as described above and commercially available from Kraton Polymers of Houston, Tex. under the trade designation KRATON®. Likewise, particularly suitable low performance elastomers include elastomeric polyolefins, such as metallocene-catalyzed polyolefins (e.g., single site metallocene-catalyzed linear low density polyethylene) commercially available from DuPont Dow Elastomers, LLC under the trade designation AFFINITY®. In some embodiments, the high performance elastomer may constitute from about 25 wt. % to about 90 wt. % of the polymer component of the film, and the low performance elastomer may likewise constitute from about 10 wt. % to about 75 wt. % of the polymer component of the film. Further examples of such a high performance/low performance elastomer blend are described in U.S. Pat. No. 6,794,024 to Walton, et al., which is incorporated herein in its entirety by reference thereto for all purposes.

As stated, the breathable film may be microporous. The micropores form what is often referred to as tortuous pathways through the film. Liquid contacting one side of the film does not have a direct passage through the film. Instead, a network of microporous channels in the film prevents liquids from passing, but allows gases and water vapor to pass. Microporous films may be formed from a polymer and a filler (e.g., calcium carbonate). Fillers are particulates or other forms of material that may be added to the film polymer extrusion blend and that will not chemically interfere with the extruded film, but which may be uniformly dispersed throughout the film. Generally, on a dry weight basis, based on the total weight of the film, the film includes from about 30% to about 90% by weight of a polymer. In some embodiments, the film includes from about 30% to about 90% by weight of a filler. Examples of such films are described in U.S. Pat. Nos. 5,843,057 to McCormack; 5,855,999 to McCormack; 5,932,497 to Morman, et al.; 5,997,981 to McCormack et al.; 6,002,064 to Kobylivker, et al.; 6,015,764 to McCormack, et al.; 6,037,281 to Mathis, et al.; 6,111,163 to McCormack, et al.; and 6,461,457 to Taylor, et al., which are incorporated herein in their entirety by reference thereto for all purposes.

The films are generally made breathable by stretching the filled films to create the microporous passageways as the polymer breaks away from the filler (e.g., calcium carbonate) during stretching. For example, the breathable material contains a stretch-thinned film that includes at least two basic components, i.e., a polyolefin polymer and filler. These components are mixed together, heated, and then extruded into a film layer using any one of a variety of film-producing processes known to those of ordinary skill in the film processing art. Such film-making processes include, for example, cast embossed, chill and flat cast, and blown film processes.

Another type of breathable film is a monolithic film that is a nonporous, continuous film, which because of its molecular structure, is capable of forming a liquid-impermeable, vapor-permeable barrier. Among the various polymeric films that fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. Without intending to be held to a particular mechanism of operation, it is believed that films made from such polymers solubilize water molecules and allow transportation of those molecules from one surface of the film to the other. Accordingly, these films may be sufficiently continuous, i.e., nonporous, to make them substantially liquid-impermeable, but still allow for vapor permeability.

Breathable films, such as described above, may constitute the entire breathable material, or may be part of a multilayer film. Multilayer films may be prepared by cast or blown film coextrusion of the layers, by extrusion coating, or by any conventional layering process. Further, other breathable materials that may be suitable for use in the present invention are described in U.S. Pat. Nos. 4,341,216 to Obenour; 4,758,239 to Yeo, et al.; 5,628,737 to Dobrin, et al.; 5,836,932 to Buell; 6,114,024 to Forte; 6,153,209 to Vega, et al.; 6,198,018 to Curro; 6,203,810 to Alemany, et al.; and 6,245,401 to Ying, et al., which are incorporated herein in their entirety by reference thereto for all purposes.

If desired, the breathable layers 14a and 14b may also contain a breathable film that is bonded to a nonwoven web, knitted fabric, and/or woven fabric using well-known techniques. For instance, suitable techniques for bonding a film to a nonwoven web are described in U.S. Pat. Nos. 5,843,057 to McCormack; 5,855,999 to McCormack; 6,002,064 to Kobylivker, et al.; 6,037,281 to Mathis, et al.; and WO 99/12734, which are incorporated herein in their entirety by reference thereto for all purposes. For example, a breathable film/nonwoven laminate material may be formed from a nonwoven layer and a breathable film layer. The layers may be arranged so that the breathable film layer is attached to the nonwoven layer. In one particular embodiment, the breathable material is formed from a nonwoven fabric (e.g., polypropylene spunbonded web) laminated to a breathable film.

As stated above, the breathable layers 14a and 14b may prevent an excessive amount of liquids from contacting the thermoregulatory substrate 12 and also allow for the permeability of oxygen and/or air. In some cases, however, the thermal covering 10 may not retain moisture long enough to allow the exothermic reaction to produce heat over an extended period of time. Thus, the thermal covering 10 may sometimes include one or more components to help retain moisture. For instance, as shown in FIGS. 1-2, the thermal covering 10 may also include an absorbent layer 16 that is configured to absorb and hold moisture for an extended period of time. The absorbent layer 16 may, for instance, include a matrix of hydrophilic fibers. In one embodiment, an absorbent web is employed that contains a matrix of cellulosic fluff fibers. One type of fluff that may be used in the present invention is identified with the trade designation CR1654, available from U.S. Alliance of Childersburg, Ala., and is a bleached, highly absorbent sulfate wood pulp containing primarily softwood fibers. Airlaid webs may also be used. In an airlaying process, bundles of small fibers having typical lengths ranging from about 3 to about 19 millimeters are separated and entrained in an air supply and then deposited onto a forming screen, usually with the assistance of a vacuum supply. The randomly deposited fibers then are bonded to one another using, for example, hot air or a spray adhesive. Another type of suitable absorbent nonwoven web is a coform material, which may be a blend of cellulose fibers and meltblown fibers.

In some embodiments, the absorbent layer 16 may contain a superabsorbent material, e.g., a water-swellable material capable of absorbing at least about 20 times its weight and, in some cases, at least about 30 times its weight in an aqueous solution containing 0.9 weight percent sodium chloride. The superabsorbent materials may be natural, synthetic and modified natural polymers and materials. In addition, the superabsorbent materials may be inorganic materials, such as silica gels, or organic compounds, such as cross-linked polymers. Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Other suitable absorbent gelling materials are disclosed in U.S. Pat. Nos. 3,901,236 to Assarsson et al.; 4,076,663 to Masuda et al.; and 4,286,082 to Tsubakimoto et al., which are incorporated herein in their entirety by reference thereto for all purposes.

When employed, the breathable layers 14a and 14b and the absorbent layer 16 may be positioned in various ways relative to the thermoregulatory substrate 12. In FIGS. 1-2, for example, the breathable layers 14a and 14b are positioned directly adjacent to the thermoregulatory substrate 12. As a result, the breathable layers 14a and 14b may prevent external liquids from contacting the substrate 12 and also control the amount of air that contacts the substrate 12 over a given period of time. The absorbent layer 16 may also be positioned in various locations, but is generally positioned to help facilitate the source of moisture for the thermoregulatory substrate 12. For example, moisture may be applied to the absorbent layer 16 prior to or during assembly of the thermal covering 10. Alternatively, moisture may be applied to the thermal covering 10 after assembly, and the absorbent layer 16 may help draw such moisture toward the thermoregulatory substrate 12. It should be understood that, although shown herein as having one absorbent layer, any number of absorbent layers (if any) may be employed in the present invention.

The thermal covering of the present invention may also contain various other optional layers and/or regions for enhancing the ability of the covering to provide heat to a patient or user. For example, in the embodiments illustrated in FIGS. 1-2, the thermal covering 10 employs a thermally conductive layer 18 to help distribute heat toward the direction of the patient/user (i.e., −z direction) and/or along the x-y plane of the covering 10, thereby improving the uniformity of heat application over a selected area. The thermally conductive layer 18 may have a coefficient of thermal conductivity of at least about 0.1 Watts per meter-Kelvin (W/m-K), and in some embodiments, from about 0.1 to about 10 W/m-k.

Although any conductive material may generally be employed, it is often desired that the selected material be conformable to enhance the comfort and flexibility of the covering 10. Suitable conformable materials include, for instance, fibrous materials (e.g., nonwoven webs), films, and so forth. Optionally, the conductive layer 18 may be vapor-permeable so that air may contact the substrate 12 when desired to activate the exothermic reaction. One type of vapor-permeable, conformable material that may be used in the conductive layer 18 is a nonwoven web material. For example, the conductive layer 18 may contain a nonwoven laminate, such as a spunbonded/meltblown/spunbonded ("SMS") laminate. Such SMS laminates may also provide liquid strike-through protection and breathability. The SMS laminate is formed by well-known methods, such as described in U.S. Pat. No. 5,213,881 to Timmons, et al., which is incorporated herein its entirety by reference thereto for all purposes. Another type of vapor-permeable, conformable material that may be used in the conductive layer 18 is a breathable film. For example, the conductive layer 18 may sometimes utilize a breathable film/nonwoven laminate.

Regardless of the materials selected, a variety of techniques may be employed to provide conductivity to the conductive layer 18. For example, in some embodiments, a metallic coating may be utilized to provide conductivity. Metals suitable for such a purpose include, but are not limited to, copper, silver, nickel, zinc, tin, palladium, lead, copper, aluminum, molybdenum, titanium, iron, and so forth. Metallic coatings may be formed on a material using any of a variety of known techniques, such as vacuum evaporation, electrolytic plating, etc. For instance, U.S. Pat. Nos. 5,656,355 to Cohen; 5,599,585 to Cohen; 5,562,994 to Abba, et al.; and 5,316,837 to Cohen, which are incorporated herein their entirety by reference thereto for all purposes, describes suitable techniques for depositing a metal coating onto a material. Besides a metal coating, still other techniques may be employed to provide conductivity. For example, in one embodiment, an additive may be incorporated into the material (e.g., fibers, film, etc.) to enhance conductivity. Examples of such additives include, but are not limited to, carbon fillers, such as carbon fibers and powders; metallic fillers, such as copper powder, steel, aluminum powder, and aluminum flakes; and ceramic fillers, such as boron nitride, aluminum nitride, and aluminum oxide. Commercially available examples of suitable conductive materials include, for instance, thermally conductive compounds available from LNP Engineering Plastics, Inc. of Exton, Pa. under the name Konduit® or from Cool Polymers of Warwick, R.I. under the name CoolPoly®. Although several examples of conductive materials have been described above, it should be understood that any known conductive material may be generally used in the present invention.

In addition to a conductive layer 18, still other optional layers may be employed to enhance the effectiveness of the thermal covering 10. For example, in the embodiments illustrated in FIGS. 1-2, an insulation layer 20 is employed to inhibit heat dissipation to the outer environment so that heat is instead focused toward the patient or user. Because the insulation layer 20 increases the overall heat-producing efficiency of the covering 10, the desired temperature increase may be reached with a lower amount of exothermic coating or other reactant (i.e., moisture or oxygen). The insulation layer 20 may have a coefficient of thermal conductivity of less than about 0.1 Watts per meter-Kelvin (W/m-K), and in some embodiments, from about 0.01 to about 0.05 W/m-k.

Generally speaking, any known insulation material may be employed in the present invention. If desired, the selected insulation material may be fibrous in nature to improve the overall conformability of the thermal covering 10. The fibrous material may possess high loft to enhance its insulative properties. Suitable high loft materials may include porous woven materials, porous nonwoven materials, etc. Particularly suitable high loft materials are nonwoven multicomponent (e.g., bicomponent) polymeric webs. For example, the multicomponent polymers of such webs may be mechanically or chemically crimped to increase loft. Examples of suitable high loft materials are described in more detail in U.S. Pat. Nos. 5,382,400 to Pike, et al.; 5,418,945 to Pike, et al. and 5,906,879 to Huntoon, et al., which are incorporated herein in their entirety by reference thereto for all purposes. Still other suitable materials for use as an insulation material are described in U.S. Pat. No. 6,197,045 to Carson, which is incorporated herein in its entirety by reference thereto for all purposes.

The thermal covering 10 may also include a bodyside layer 22 and an environment-side layer 24 that form the outer surfaces 17 and 19, respectively, of the thermal covering 10. For example, the layers 22 and 24 may present a compliant, soft feeling, and non-irritating surface to the user's skin. The layers 22 and 24 may be formed from a wide variety of materials depending on the particular configuration of the covering 10. For example, the layers 22 may be formed from materials that are liquid- and vapor-permeable, liquid-impermeable and vapor-permeable ("breathable"), and so forth. If desired, woven and/or nonwoven fabrics are used for the layers 22 and 24. For example, the layers 22 and 24 may be formed from a meltblown or spunbonded web of polyolefin fibers. The layers 22 and 24 may also be a bonded-carded web of natural and/or synthetic fibers. The layers 22 and 24 may further include a composition that is configured to transfer to the wearer's skin for improving skin health. Suitable compositions are described in U.S. Pat. No. 6,149,934 to Krzysik et al., which is incorporated herein in its entirety by reference thereto for all purposes.

The various layers and/or components of the thermal covering 10 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In some embodiments, the exothermic coating may serve the dual purposes of generating heat and also acting as the adhesive. For example, the binder of the exothermic coating may bond together one or more layers of the thermal covering 10.

Figure 3:
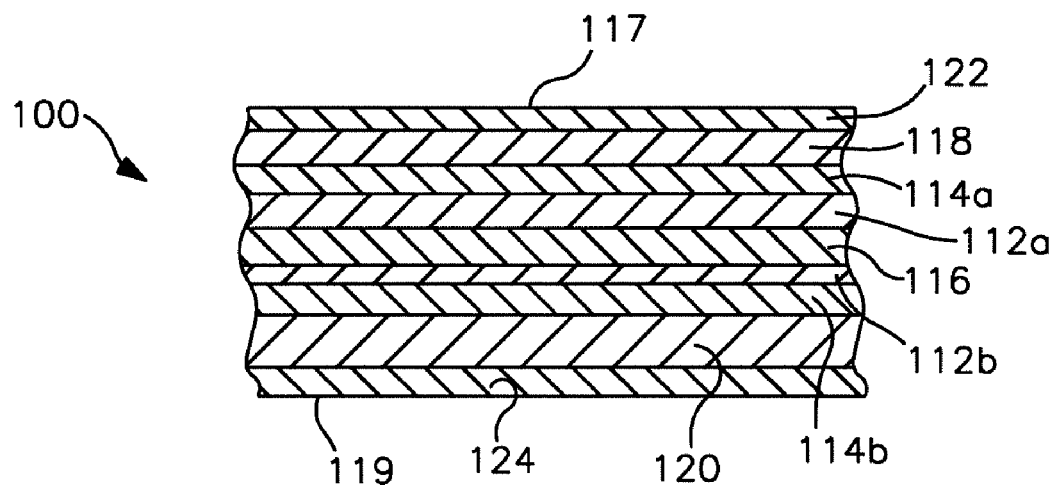
FIG. 3 illustrates a cross-sectional view of another embodiment of a thermal covering of the present invention.

To further enhance the amount of heat generated by the thermal covering, multiple thermoregulatory substrates may sometimes by employed. The multiple thermoregulatory substrates may be placed adjacent to one another or spaced apart by one or more layers. For example, referring to FIG. 3, one embodiment of a thermal covering 100 is shown that contains a first thermoregulatory substrate 112a and a second thermoregulatory substrate 112b. Although not required, the thermal covering 100 also includes a first breathable layer 114a and a second breathable layer 114b. The thermal covering 100 also includes an absorbent layer 116 for facilitating the supply of moisture to the thermoregulatory substrates 112a and 112b. The absorbent layer 116 is positioned between the thermoregulatory substrate 112a/breathable layer 114a and the thermoregulatory substrate 112b/breathable layer 114b. In this manner, the amount of moisture supplied to each substrate is relatively uniform. It should be understood, however, that any placement, selection, and/or number of layers may be employed in the present invention. In addition, as described above, the thermal covering 100 may also include a conductive layer 118, an insulation layer 120, a bodyside layer 122, and an environment-side layer 124. The bodyside layer 122 and environment-side layer 124 define outer surfaces 117 and 119, respectively, of the thermal covering 100.

Although various configurations of a thermal covering have been described above, it should be understood that other configurations are also included within the scope of the present invention. For instance, other layers may also be employed to improve the exothermic properties of the thermal covering. For example, a substrate may be used near or adjacent to the coated substrate of the present invention that includes a coating of moisture-retaining particles. As described above, the moisture-retaining particles may retain and release moisture for activating the exothermic reaction. Furthermore, of particular benefit, one or more of the above-mentioned layers may accomplish multiple functions of the thermal covering. For example, in some embodiments, the bodyside layer may present a soft and compliant surface to a user, while simultaneously serving as a breathable layer for regulating the amount of moisture and air that contacts the thermoregulatory substrate. In other embodiments, a conductive or insulation layer of the thermal covering may also serve as a breathable or absorbent layer. Furthermore, the breathable layer, absorbent layer, etc., may be coated with an exothermic coating and thus also serve as a thermoregulatory substrate. Although not expressly set forth herein, it should be understood that numerous other possible combinations and configurations would be well within the ordinary skill of those in the art.

As stated above, moisture is used to initiate the exothermic reaction. The moisture may be absorbed from the surrounding environment. Likewise, moisture may be applied as an additional activation step using various techniques, such as spraying, dipping, coating, dropping (e.g., using a syringe), etc. Although the amount of moisture applied may vary depending on the reaction conditions and the amount of heat desired, moisture may sometimes be added in an amount from about 20 wt. % to about 500 wt. %, and in some embodiments, from about 50 wt. % to about 200 wt. %, of the weight of the amount of oxidizable metal present in the coating. In any event, a sufficient amount of moisture is employed to activate an exothermic, electrochemical reaction between the electrochemically oxidizable element (e.g., metal powder) and the electrochemically reducible element (e.g., oxygen). Moisture may be applied any time prior to or during use of the thermal covering, such as just prior to use or during the manufacture of the thermal covering. For example, water may be pre-applied to an absorbent layer of the thermal covering that provides the source of moisture for the exothermic reaction. Although not necessarily required, it may be desired to seal such water-treated thermal coverings within an enclosure (e.g., film) that inhibits the substrate from contacting enough oxygen to prematurely activate the exothermic reaction. To generate heat, the thermal covering is simply removed from the package and exposed to air.

In use, one or more outer surfaces defined by the thermal covering may be capable of reaching a temperature of from about 30° C. to about 60° C., in some embodiments from about 35° C. to about 50° C., and in some embodiments from about 37° C. to about 43° C. Desirably, such temperature ranges are maintained for at least about 1 hour, in some embodiments at least about 2 hours, in some embodiments at least about 4 hours, and in some embodiments, at least about 10 hours (e.g., for overnight use). For example, in a surgical setting, the thermal covering may be provided in the configuration of a surgical drape, blanket, or garment. Medical personnel may remove the thermal covering from any optional packaging and then place it on the desired patient surface so that the thermal effect is transferred to the patient. Thereafter, surgical procedures may be performed on exposed portions of the patient or through a fenestration in the drape without risk of hypothermia. One skilled in the art will recognize that the specific description of the thermal covering is exemplary, and that other embodiments may incorporate additional features.

The present invention may be better understood with reference to the following examples.

Example 1

The ability to form a warmth-providing substrate in accordance with the present invention was demonstrated. Initially, a bonded carded web fabric was provided that had a size of 8" by 11" and a basis weight of 1.5 ounces per square yard. The fabric was formed from a blend of 60 wt. % bicomponent fibers and 40 wt. % polyester fibers. The bicomponent fibers were obtained from Fibervisions, Inc. of Covington, Ga. under the name "ESC 215", which had a polyethylene sheath and polypropylene core, a denier of 1.5, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. Initially, 420.0 grams of iron powder and 22.1 grams of sodium chloride (Mallinckrodt) were slowly added to 500 grams of activated carbon ink while stirring. The iron powder was obtained from Sigma-Aldrich Co. of St. Louis, Mo. and had a particle size of −325 mesh and a metal purity of 97%. The activated carbon ink was obtained from MeadWestvaco Corp of Stamford, Conn. under the name "DPX-8433-68A", and contained 14 wt. % activated carbon, 22 wt. % styrene acrylic binder, and 64 wt. % water. The percent solids of the resulting mixture was determined to be 65.9%. The calculated concentration of each component of the aqueous formulation is set forth below in Table 1.

TABLE 1

Components of the Aqueous Formulation

| Component | Calculated Amount |
|---|---|
| Iron | 44.6% |
| Activated Carbon | 7.3% |
| Binder | 11.5% |
| Sodium Chloride | 2.4% |
| Water | 34.2% |

One side of the fabric was coated with the formulation using a #60 single wound metering rod. After applying the aqueous formulation, the coated fabric was dried in a forced air oven at 110° C. for about 15 minutes. The concentration of the components of the exothermic coating was then calculated from the initial fabric weight (4.5 grams), the dry coated fabric weight (73.2 grams), and the composition of the aqueous formulation. The results are set forth below in Table 2.

TABLE 2

Components of the Exothermic Coating

| Component | Calculated Amount |
|---|---|
| Iron | 67.9% |
| Activated Carbon | 11.1% |
| Binder | 17.4% |
| Sodium Chloride | 3.6% |
| Solids Add-On Level | ~1530% |

To test the effectiveness of the coated fabric in providing warmth, two pieces of the coated fabric (2"×2.5") were provided that had a total weight of 6.21 grams. A five-layered structure was designed to activate the exothermic reaction. Specifically, the five-layered structure included the two fabric pieces as first and second outer layers; two vermiculite-coated fabrics as third and fourth layers, each of which was positioned adjacent to the first and second outer layers, respectively; and an absorbent layer as a fifth layer positioned between the third and fourth layers. The iron coating on the first and second outer layers faced away from the absorbent layer, and the particle coating of the third and fourth layers faced toward the absorbent layer.

The absorbent layer was formed from 60 wt. % fluff and 40 wt. % superabsorbent, and had a basis weight of 250 grams per square meter and a size of 2"×2.5". The fluff was obtained from U.S. Alliance of Childersburg, Ala. under the name "CR1654", and was a bleached, highly absorbent sulfate wood pulp containing primarily softwood fibers. The superabsorbent was obtained from Degussa AG under the name "FAVOR® 9543." The vermiculite-coated layers (third and fourth layers) were formed from a bonded carded web fabric having a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish. The vermiculite coating was formed by adding ground vermiculite to an activated carbon ink obtained from MeadWestvaco under the name "DPX-8433-68A." The fabric was coated on one side with the coating, which contained 18.6 wt. % vermiculite, 31.4 wt. % activated carbon, and 50 wt. % binder. The solids add-on level of the coating was 606%.

Figure 4:
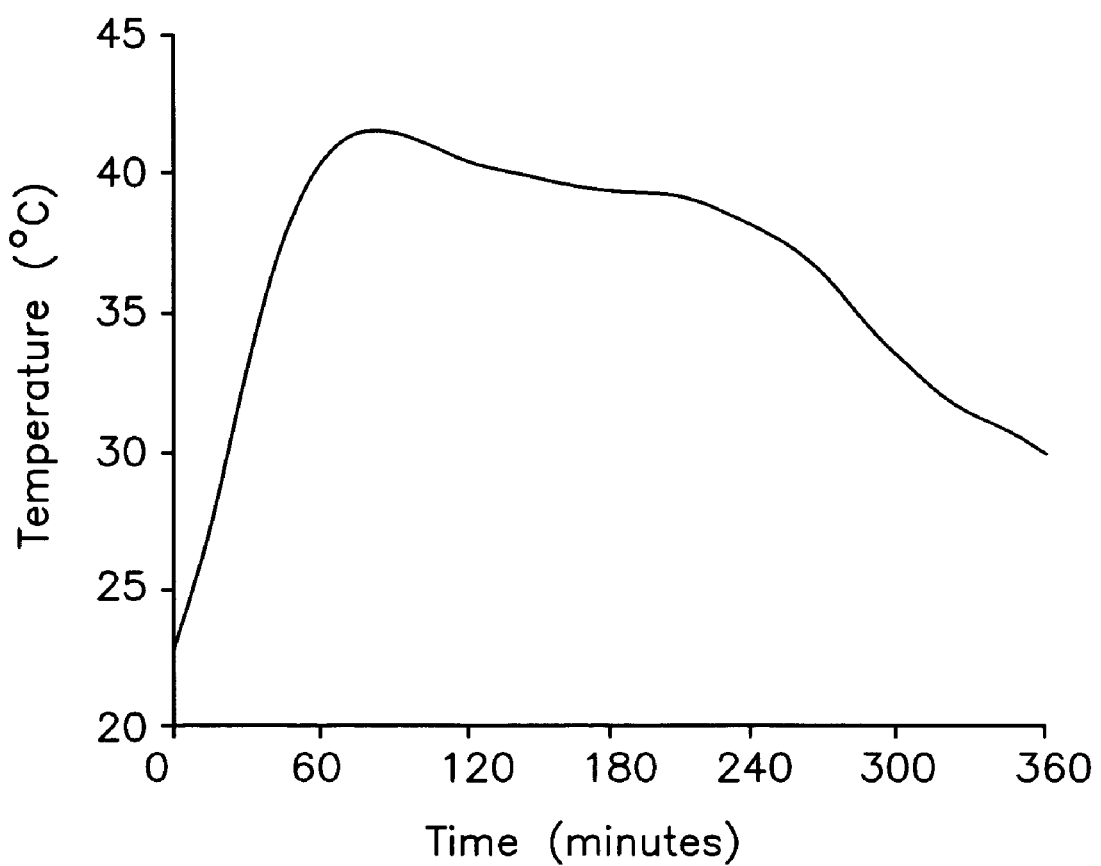
FIG. 4 is a thermal response curve showing temperature versus time for the sample of Example 1.

Prior to forming the multi-layered structure, the absorbent layer was wetted by spraying a fine mist of water to each side so that the weight increased from 0.9 gram to 5.5 grams. This five-layered structure was then placed inside of an empty MYCOAL® pouch (available from Mycoal Warmers Co., Ltd. of Tochigi, Japan), which had been opened at one edge to remove the powder contents. The pouch was then sealed and a thermocouple wired to a data collection device was attached to one side of the pouch. The temperature was recorded as a function of time (at 1-second intervals) to give a thermal curve, which is shown in FIG. 4. As illustrated, the iron-coated fabric provided warmth (38° C. to 42° C.) for at least 3 hours.

Example 2

The ability to form a warmth-providing substrate in accordance with the present invention was demonstrated. Initially, a bonded carded web fabric was provided that had a size of 7" by 12.5" and a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 400-milliliter pyrex beaker, 5.0 grams of "Metolose SM4000" (methyl cellulose, available from Shin-Etsu Chemical Co., Ltd.) and 12.5 grams of sodium chloride (Mallinckrodt) were added to 151.8 grams of warm (ca. 70° C.) distilled water while stirring. Thereafter, 51.9 grams of an aqueous calcium carbonate slurry was added to the formulation while stirring. The aqueous calcium carbonate slurry was obtained from Omya, Inc. under the name "XC4900" and had a solids content of 40.7%. Thereafter, 170.0 grams of iron powder and 15.0 grams of activated carbon powder were added to the formulation. The iron powder was obtained from Sigma-Aldrich Co. of St. Louis, Mo. and had a particle size of −325 mesh and a metal purity of 97%. The activated carbon was obtained from MeadWestvaco Corp. under the name "Nuchar SA-20." This final formulation was stirred for about 30 minutes and then the beaker was placed in an ice bath to cool and increase the viscosity. The viscosity was observed to increase dramatically when the temperature of the formulation reached about 17° C. The ice bath was removed and the formulation was manually stirred with a spatula as it warmed up to about room temperature and was then used to coat the fabric. The calculated concentration of each component of the aqueous formulation is set forth below in Table 3.

TABLE 3

Components of the Aqueous Formulation

| Component | Calculated Amount |
|---|---|
| Iron | 41.9% |
| Activated Carbon | 3.7% |
| Binder | 1.2% |
| Calcium Carbonate | 5.2% |
| Sodium Chloride | 3.1% |
| Water | 44.9% |

One side of the fabric was coated with the formulation using a #60 single wound metering rod. After applying the aqueous formulation, the coated fabric was then dried in a forced air oven at 110° C. for about 15 minutes. The concentration of the components of the exothermic coating was then calculated from the initial fabric weight (2.0 grams), the dry coated fabric weight (20.5 grams), and the composition of the aqueous formulation. The results are set forth below in Table 4.

TABLE 4

Components of the Exothermic Coating

| Component | Calculated Amount |
|---|---|
| Iron | 76.1% |
| Activated Carbon | 6.7% |
| Binder | 2.2% |
| Calcium Carbonate | 9.4% |
| Sodium Chloride | 5.6% |
| Solids Add-On Level | ~925% |

The coated fabric was observed to have a medium gray color and very good drape characteristics. Further, to test the effectiveness of the coated fabric in providing warmth, four pieces of the coated fabric (3.5"×4") were provided that had a total weight of 12.67 grams. A five-layered structure was designed to activate the exothermic reaction. Specifically, the five-layered structure included two of the coated fabric pieces positioned on one side of an absorbent layer, and the other two coated fabric pieces positioned on the other side of the absorbent layer. The iron coating on each coated fabric faced away from the absorbent layer. The absorbent layer was formed from 60 wt. % fluff and 40 wt. % superabsorbent, and had a basis weight of 250 grams per square meter and a size of 3.5"×4". The fluff was obtained from U.S. Alliance of Childersburg, Ala. under the name "CR1654", and was a bleached, highly absorbent sulfate wood pulp containing primarily softwood fibers. The superabsorbent was obtained from Degussa AG under the name "FAVOR® 9543." Prior to forming the multi-layered structure, the absorbent layer was wetted by spraying a fine mist of water to each side so that the weight increased from 2.83 grams to 14.42 grams.

This five-layered structure was then placed inside of a rectangular pouch (4.5" by 5") made from two spunbond-film laminates and an aluminum-coated SMS. The spunbond web of each laminate had a basis weight of 0.5 ounces per square yard, was formed from polypropylene, and was necked 50% prior to lamination. The breathable film of each laminate was a microporous film formed from 33 wt. % of an S-EP-S elastomeric block copolymer available from Kuraray Company, Ltd. of Okayama, Japan under the trade name SEPTON®; 16.75 wt. % of linear low density polyethylene; and 50.25 wt. % of a calcium carbonate filler. The film was adhesively laminated to the spunbond web. Methods for forming such a spunbond/film laminate are described in U.S. Pat. No. 6,794,024 to Walton, et al.

Figure 5:
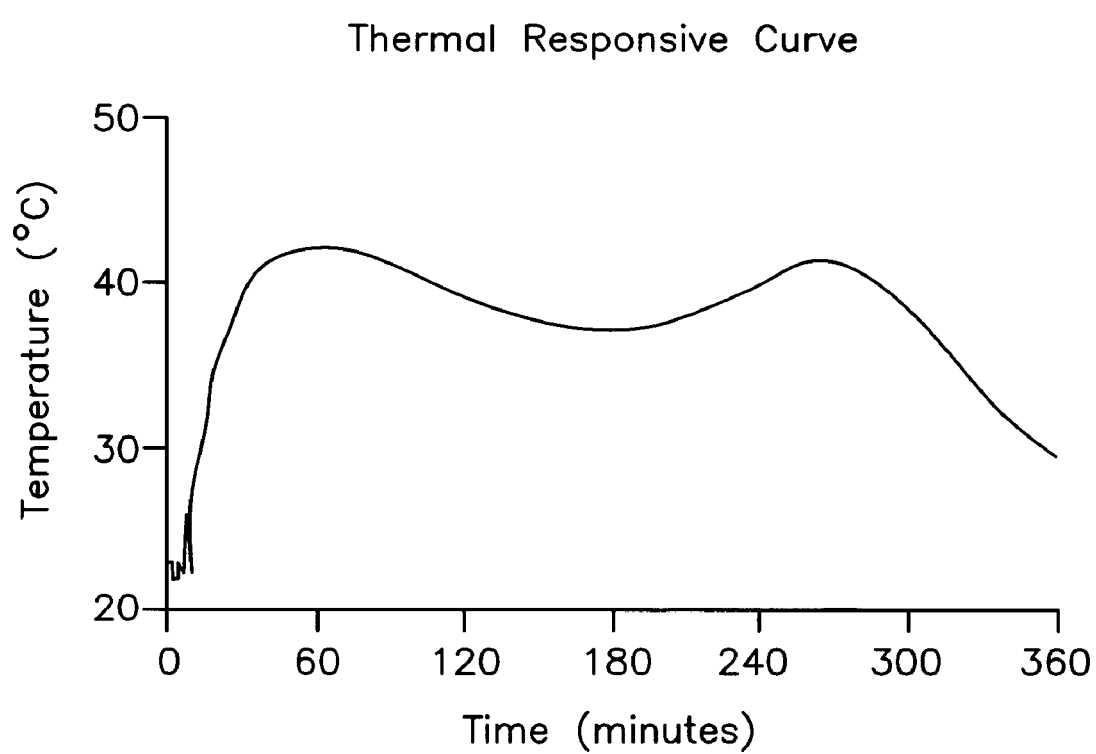
FIG. 5 is a thermal response curve showing temperature versus time for the sample of Example 2.

The aluminum-coated SMS was used as the outside layer of the pouch, and all of the pouch layers were tacked together with an adhesive spray. The WVTR of the pouch containing the five-layered structure was determined to be 375 g/m$^2$/24 hrs. The pouch was then sealed and a thermocouple wired to a data collection device was attached to one side of the pouch. The temperature was recorded as a function of time (at 3-second intervals) to give the thermal curve shown in FIG. 5. As illustrated, the iron-coated fabric provided warmth (38° C. to 42° C.) for at least 4 hours.

Example 3

The ability to form a warmth-providing substrate in accordance with the present invention was demonstrated. Initially, a 14"-wide roll of a bonded carded web fabric was provided that had a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 2-gallon metal pail, 2,562.7 grams of iron powder and 134.2 grams of sodium chloride (Mallinckrodt) were slowly added to 3,047.7 grams of activated carbon ink while stirring. The iron powder was obtained from North American Höganäs under the name "AC-325" and had a particle size of −325 mesh. The activated carbon ink was obtained from MeadWestvaco Corp of Stamford, Conn. under the name "DPX-8433-68B", and contained 14 wt. % activated carbon, 22 wt. % styrene acrylic binder, and 64 wt. % water. The percent solids of the resulting mixture was determined to be 66%. The calculated concentration of each component of the aqueous formulation is set forth below in Table 5.

TABLE 5

Components of the Aqueous Formulation

| Component | Calculated Amount |
|---|---|
| Iron | 44.6% |
| Activated Carbon | 7.2% |
| Binder | 11.4% |
| Sodium Chloride | 2.3% |
| Water | 34.5% |

The aqueous formulation was applied to both sides of the fabric at a rate of about 10 feet per minute. Specifically, the fabric was saturated with the formulation by applying it to the top side from a plastic tube "shower" and to the bottom side by an applicator roll that picked up the composition from a metal pan. The saturated fabric was nipped at a pressure of 60 psig and then dried over four steam cans (measured temperatures of 117.7° C., 118.3° C., 112.8° C., and 121.1° C.). The concentration of the components of the exothermic coating was then calculated from a 14"×18" piece of the treated fabric (28.80 grams), a 14"×18" piece of an untreated fabric (5.45 grams), and the composition of the aqueous formulation. The results are set forth below in Table 6.

TABLE 6

Components of the Exothermic Coating

| Component | Calculated Amount |
|---|---|
| Iron | 67.9% |
| Activated Carbon | 11.1% |
| Binder | 17.4% |
| Sodium Chloride | 3.6% |
| Solids Add-On Level | ~428% |

A seven-layered structure (3.5'×5') was then designed for activating the exothermic reaction. Specifically, the seven-layered structure included three of the coated fabric pieces positioned on one side of an absorbent layer, and the other three coated fabric pieces positioned on the other side of the absorbent layer. The absorbent layer was formed from 40 wt. % wood pulp fluff, 50 wt. % superabsorbent, and 10 wt. % of "ESC 806" PE/PP bicomponent fibers (Fibervisions, Inc.). The absorbent layer had a basis weight of 300 grams per square meter and a density of 0.18 grams per cubic centimeter. The wood pulp fluff was obtained from Weyerhaeuser under the name "NB416." The superabsorbent was obtained from Degussa AG under the name "SXM 9394." Prior to forming the multi-layered structure, the absorbent layer was wetted by spraying a fine mist of water to each side in an amount of 4 parts water to 1 part fabric. This seven-layered structure was then placed inside of a rectangular pouch made from three spunbond-film laminates (as described in Example 2) and an aluminum-coated SMS. The aluminum-coated SMS was used as the outside layer of the pouch, and all of the pouch layers were tacked together with an adhesive spray and sealed around the edges.

In addition to the above-described design, another seven-layered structure (6"×6") was also designed. Specifically, the seven-layered structure had the same construction as described above, except that the absorbent layer was formed from 75 wt. % wood pulp fluff, 15 wt. % superabsorbent, and 10 wt. % of "ESC 806" PE/PP bicomponent fibers (Fibervisions, Inc.). The absorbent layer had a basis weight of 120 grams per square meter and a density of 0.12 grams per cubic centimeter. The wood pulp fluff was obtained from Weyerhaeuser under the name "NB416." The superabsorbent was obtained from Degussa AG under the name "SXM 9394." Prior to forming the multi-layered structure, the absorbent layer was wetted by spraying a fine mist of water to each side in an amount of 3 parts water to 1 part fabric. This seven-layered structure was placed inside of a rectangular pouch made from two layers of a spunbond-film laminate and one layer of an aluminum-coated SMS. The aluminum-coated SMS was used as the outside layer of the pouch, and all of the pouch layers were tacked together with an adhesive spray and sealed around the edges. Prolonged warming characteristics were qualitatively observed upon exposure to air.

Example 4

The ability to form a warmth-providing substrate in accordance with the present invention was demonstrated. Initially, a two-layered fabric was provided that had a size of 8" by 12.5" and a basis weight of 2.3 ounces per square yard. One layer of the fabric was formed from bicomponent fibers obtained from Fibervisions, Inc. of Covington, Ga. under the name "ESC 215", which had a polyethylene sheath and polypropylene core, a denier of 1.5, and 0.55 wt. % "HR6" finish. The other layer of the fabric was formed from a blend of 25 wt. % polyester fibers (obtained from Invista of Wichita, Kans. under the name "T-295", denier of 6.0, 0.50% L1 finish) and 75 wt. % of the "ESC 215" PE/PP bicomponent fibers.

The coating formulation was prepared as described in Example 2. Thereafter, the polyester/bicomponent layer of the fabric was coated with the exothermic coating using a #60 single wound metering rod. After applying the aqueous formulation, the coated fabric was then dried in a forced air oven at 110° C. for about 45 minutes. The concentration of the components of the exothermic coating was then calculated from the initial fabric weight (4.9 grams), the dry coated fabric weight (54.8 grams), and the composition of the aqueous formulation. The results are set forth below in Table 7.

TABLE 7

Components of the Exothermic Coating

| Component | Calculated Amount |
|---|---|
| Iron | 76.1% |
| Activated Carbon | 6.7% |
| Binder | 2.2% |
| Calcium Carbonate | 9.4% |
| Sodium Chloride | 5.6% |
| Solids Add-On Level | ~1018% |

The coated fabric was observed to have a medium gray color and very good drape characteristics. Further, to test the effectiveness of the coated fabric in providing warmth, two pieces of the coated fabric (3.5"×4") were provided that had a total weight of 14.38 grams. A three-layered structure was designed to activate the exothermic reaction. Specifically, the three-layered structure included an absorbent layer positioned between the two coated fabric pieces. The iron coating on each coated fabric faced away from the absorbent layer. The absorbent layer was formed from 60 wt. % fluff and 40 wt. % superabsorbent, and had a basis weight of 250 grams per square meter, a density of 0.2 grams per cubic centimeter, and a size of 3.5"×4". The fluff was obtained from U.S. Alliance of Childersburg, Ala. under the name "CR1654", and was a bleached, highly absorbent sulfate wood pulp containing primarily softwood fibers. The superabsorbent was obtained from Degussa AG under the name "FAVOR® 9543." Prior to forming the multi-layered structure, the absorbent layer was wetted by spraying a fine mist of water to each side so the weight increased from 3.11 grams to 15.97 grams.

Figure 6:
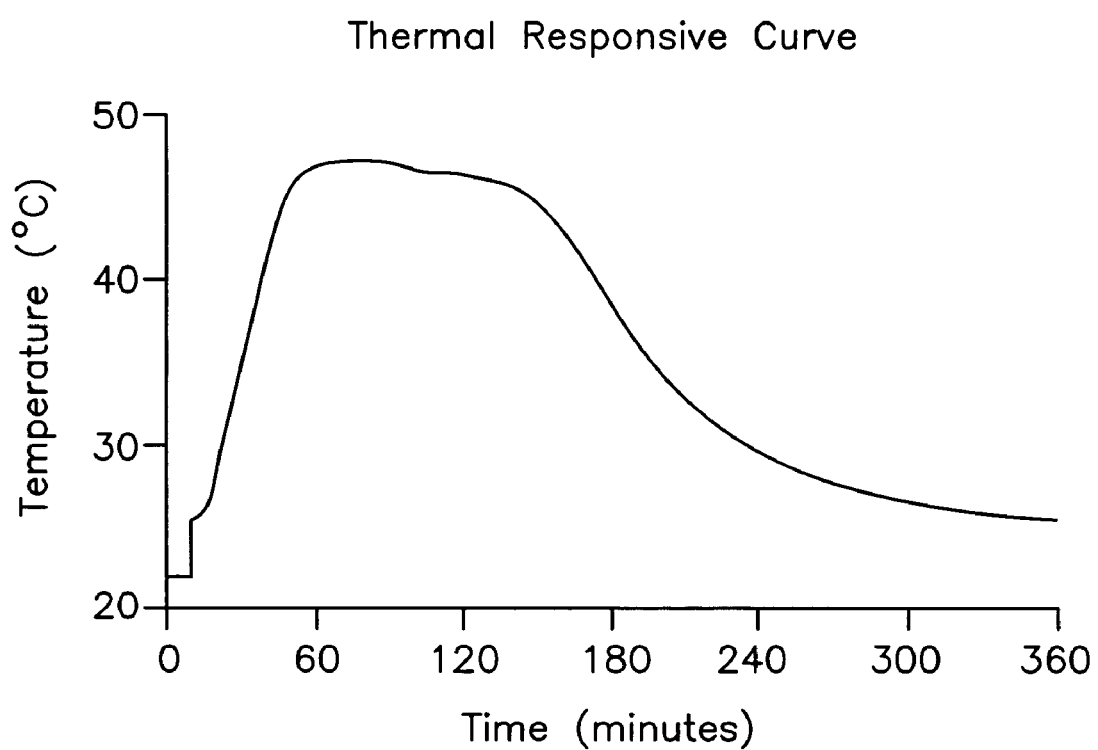
FIG. 6 is a thermal response curve showing temperature versus time for the sample of Example 4.

This three-layered structure was then placed inside of a rectangular pouch (4.5" by 4") made from three spunbond-film laminates (as described in Example 2) and an aluminum-coated SMS. The aluminum-coated SMS was used as the outside layer of the pouch, and all of the pouch layers were tacked together with an adhesive spray. The WVTR of the pouch containing the three-layer structure was determined to be 293 g/m²/24 hrs. The pouch was then sealed and a thermocouple wired to a data collection device was attached to one side of the pouch. The temperature was recorded as a function of time (at 3-second intervals) to give a thermal curve, which is shown in FIG. 6. As illustrated, the iron-coated fabric provided warmth (46° C. to 48° C.) for at least 2 hours.

Example 5

The ability to form a warmth-providing substrate in accordance with the present invention was demonstrated. Initially, a bonded carded web fabric was provided that had a size of 7" by 12.5" and a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 400-milliliter pyrex beaker, 5.0 grams of "Culminal MC 2000" (methyl cellulose, available from Hercules) and 12.6 grams of sodium chloride (Mallinckrodt) were added to 149.4 grams of warm (ca. 70° C.) distilled water while stirring. The methyl cellulose particles did not dissolve or disperse well in the warm water so it was cooled with an ice bath to about 14° C. to form a clear viscous solution. Thereafter, 48.3 grams of an aqueous slurry of calcium carbonate particles was added to the formulation while stirring. The aqueous calcium carbonate slurry was obtained from Omya, Inc. under the name "XC4900" and had a solids content of 27.7%. Thereafter, 170.0 grams of iron powder and 15.0 grams of activated carbon powder were added to the formulation. The iron powder was obtained from North American Höganäs under the name "Nutrafine RS" and had a particle size of −325 mesh. The activated carbon was obtained from MeadWestvaco Corp. under the name "Nuchar SA-20." The final viscosity was 1,402,000 centipoise (Brookfield DV-I viscometer with LV-4 spindle at 0.3 RPM) and the solids content was 56.3%. The calculated concentration of each component of the aqueous formulation is set forth below in Table 8.

TABLE 8

Components of the Aqueous Formulation

| Component | Calculated Amount |
|---|---|
| Iron | 42.5% |
| Activated Carbon | 3.8% |
| Binder | 1.3% |
| Calcium Carbonate | 3.3% |
| Sodium Chloride | 3.2% |
| Water | 45.9% |

One side of the fabric was coated with the formulation using a #60 single wound metering rod. After applying the aqueous formulation, the coated fabric was then dried in a forced air oven at 110° C. for about 15 minutes. The concentration of the components of the exothermic coating was then calculated from the initial fabric weight (2.0 grams), the dry coated fabric weight (17.9 grams), and the composition of the aqueous formulation. The results are set forth below in Table 9.

TABLE 9

Components of the Exothermic Coating

| Component | Calculated Amount |
|---|---|
| Iron | 78.7% |
| Activated Carbon | 6.9% |
| Binder | 2.4% |
| Calcium Carbonate | 6.2% |
| Sodium Chloride | 5.8% |
| Solids Add-On Level | ~795% |

The coated fabric was observed to have a medium gray color and very good drape characteristics. Further, to test the effectiveness of the coated fabric in providing warmth, four pieces of the coated fabric (3.5"×4") were provided that had a total weight of 11.34 grams. A five-layered structure was designed to activate the exothermic reaction. Specifically, the five-layered structure included two of the coated fabric pieces positioned on one side of an absorbent layer, and the other two coated fabric pieces positioned on the other side of the absorbent layer. The iron coating on each coated fabric faced away from the absorbent layer. The absorbent layer was formed from 75 wt. % wood pulp fluff, 15 wt. % superabsorbent, and 15 wt. % of "ESC 806" PE/PP bicomponent fibers (Fibervisions, Inc.). The absorbent layer had a basis weight of 120 grams per square meter and a density of 0.12 grams per cubic centimeter. The wood pulp fluff was obtained from Weyerhaeuser under the name "NB416." The superabsorbent was obtained from Degussa AG under the name "SXM 9394." Prior to forming the multi-layered structure, the absorbent layer was wetted by spraying a fine mist of water to each side in an amount of 4 parts water to 1 part fabric.

Figure 7:
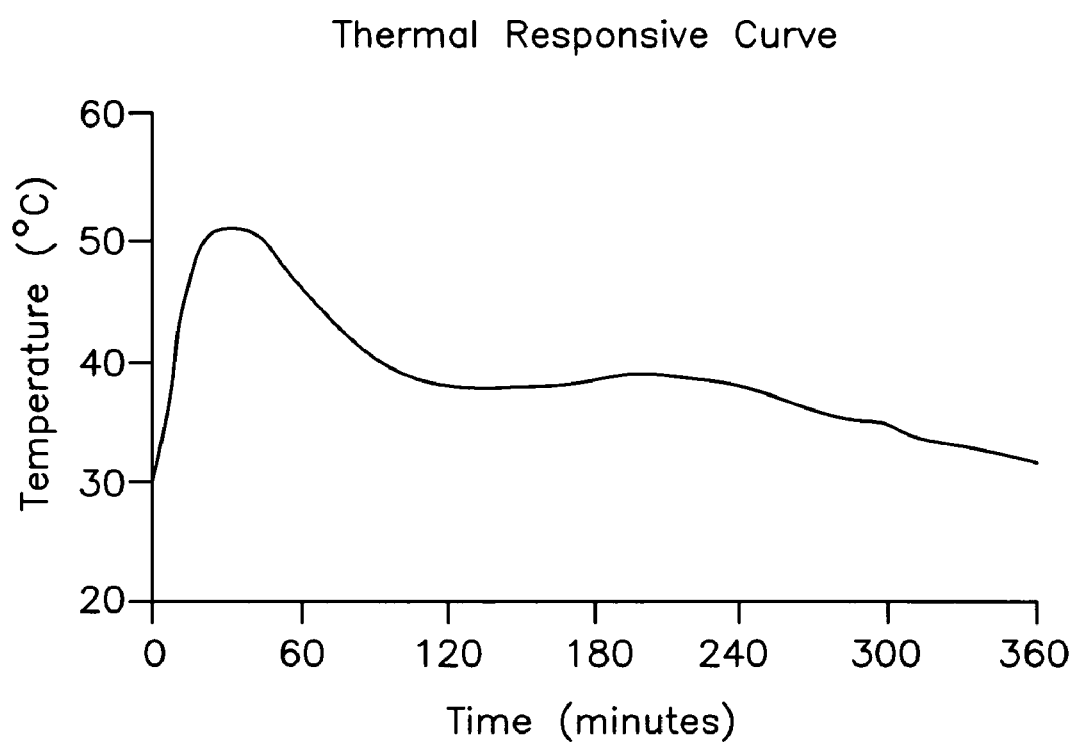
FIG. 7 is a thermal response curve showing temperature versus time for the sample of Example 5.

This five-layered structure was then placed inside of a rectangular pouch (4.5" by 4") made from two spunbond-film laminates (as described in Example 2) and an aluminum-coated SMS. The aluminum-coated SMS was used as the outside layer of the pouch, and all of the pouch layers were tacked together with an adhesive spray. The WVTR of the pouch containing the five-layered structure was determined to be 375 g/m²/24 hrs. The pouch was then sealed and a thermocouple wired to a data collection device was attached to one side of the pouch. The temperature was recorded as a function of time (at 3-second intervals) to give the thermal curve shown in FIG. 7. As illustrated, the iron-coated fabric provided warmth (38° C. to 52° C.) for at least 4 hours.

Example 6

The ability to form a warmth-providing substrate in accordance with the present invention was demonstrated. Initially, a bonded carded web fabric was provided that had a size of 7" by 12.5" and a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 400-milliliter pyrex beaker, 5.0 grams of "Bermocoll E230 FQ" (ethylhydroxyethyl cellulose from Akzo Nobel) and 12.5 grams of sodium chloride (Mallinckrodt) were added to 150.4 grams of distilled water (ca. 58° C.) while stirring. After cooling in an ice bath to a temperate of about 18° C., the solution had a viscosity of 735 centipoise (Brookfield DV-I viscometer with LV-2 spindle at 12 RPM) and a solids content of 10.4%. Thereafter, 104.6 grams of an aqueous slurry of calcium carbonate particles was added to the formulation while stirring. The aqueous calcium carbonate slurry was obtained from Omya, Inc. under the name "XC4900" and had a solids content of 28.3%. After adding the calcium carbonate slurry, the formulation had a viscosity of 1042 centipoise and a solids content of 17.4%. Thereafter, 212.8 grams of iron powder and 25.2 grams of activated carbon powder were then added to the formulation. The iron powder was obtained from North American Höganäs under the name "AC 325" and had a particle size of −325 mesh. The activated carbon was obtained from MeadWestvaco Corp. under the name "Nuchar SA-20." The final viscosity (Brookfield DV-I viscometer with LV-4 spindle at 1.5 RPM) was 185,200 centipoise and the solids content was 58.3%. The calculated concentration of each component of the aqueous formulation is set forth below in Table 10.

TABLE 10

Components of the Aqueous Formulation

| Component | Calculated Amount |
|---|---|
| Iron | 41.7% |
| Activated Carbon | 4.9% |
| Binder | 1.0% |
| Calcium Carbonate | 5.8% |
| Sodium Chloride | 2.5% |
| Water | 44.1% |

One side of the fabric was coated with the formulation using a #60 single wound metering rod. After applying the aqueous formulation, the coated fabric was then dried in a forced air oven at 110° C. for 10 to 15 minutes. The concentration of the components of the exothermic coating was then calculated from the initial fabric weight (2.1 grams), the dry coated fabric weight (20.2 grams), and the composition of the aqueous formulation. The results are set forth below in Table 11.

TABLE 11

Components of the Exothermic Coating

| Component | Calculated Amount |
|---|---|
| Iron | 74.7% |
| Activated Carbon | 8.8% |
| Binder | 1.8% |
| Calcium Carbonate | 10.4% |
| Sodium Chloride | 4.3% |
| Solids Add-On Level | ~862% |

The coated fabric was observed to have a medium gray color and very good drape characteristics. Further, to test the effectiveness of the coated fabric in providing warmth, four pieces of the coated fabric (3.5"×4") were provided that had a total weight of 11.93 grams. A five-layered structure was designed to activate the exothermic reaction. Specifically, the five-layered structure included two of the coated fabric pieces positioned on one side of an absorbent layer, and the other two coated fabric pieces positioned on the other side of the absorbent layer. The iron coating on each coated fabric faced away from the absorbent layer. The absorbent layer was formed from 40 wt. % wood pulp fluff, 50 wt. % superabsorbent, and 10 wt. % of "ESC 806" PE/PP bicomponent fibers (Fibervisions, Inc.). The absorbent layer had a basis weight of 300 grams per square meter and a density of 0.18 grams per cubic centimeter. The wood pulp fluff was obtained from Weyerhaeuser under the name "NB416." The superabsorbent was obtained from Degussa AG under the name "SXM 9394." Prior to forming the multi-layered structure, the absorbent layer was wetted by spraying a fine mist of water to each side in an amount of 2.5 parts water to 1 part fabric.

Figure 8:
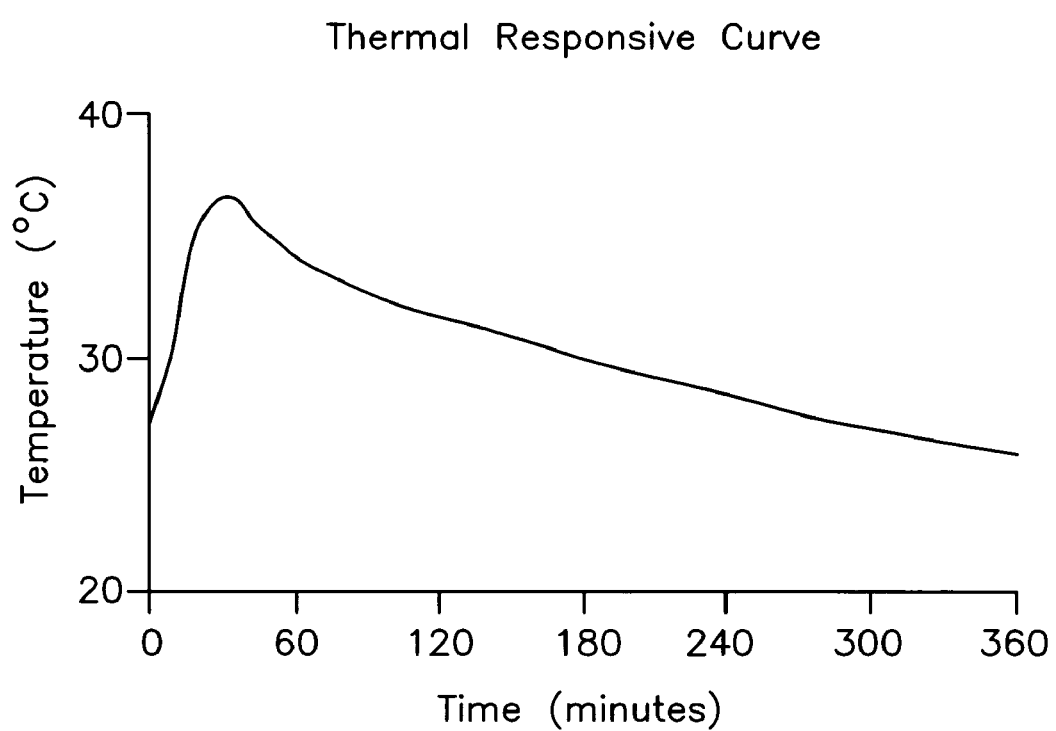
FIG. 8 is a thermal response curve showing temperature versus time for the sample of Example 6.

This five-layered structure was then placed inside of a rectangular pouch (4.5" by 4") made from two spunbond-film laminates (as described in Example 2) and an aluminum-coated SMS. The aluminum-coated SMS was used as the outside layer of the pouch, and all of the pouch layers were tacked together with an adhesive spray. The WVTR of the pouch was determined to be 375 grams/m$^2$/24 hrs. The pouch was then sealed and a thermocouple wired to a data collection device was attached to one side of the pouch. The temperature was recorded as a function of time (at 3-second intervals) to give the thermal curve shown in FIG. 8. As illustrated, the iron-coated fabric provided warmth (30° C. to 37° C.) for at least 3 hours.

Example 7

The ability to form a warmth-providing substrate in accordance with the present invention was demonstrated. Initially, a bonded carded web fabric was provided that had a size of 7" by 12.5" and a basis weight of 0.9 ounces per square yard. The fabric was formed from a blend of 75 wt. % bicomponent fibers and 25 wt. % polyester fibers. The bicomponent fibers were obtained from Fibervisions, Inc. of Covington, Ga. under the name "ESC 215", which had a polyethylene sheath and polypropylene core, a denier of 3.0, and 0.55 wt. % "HR6" finish. The polyester fibers were obtained from Invista of Wichita, Kans. under the name "T-295", which had a denier of 6.0 and contained a 0.5 wt. % L1 finish.

The coating formulation was prepared as follows. In a 1-liter metal beaker, 210.0 grams of M100 iron powder (available from North American Höganäs) and 11.0 grams of sodium chloride (Mallinckrodt) were added to 251.1 grams of activated carbon ink while stirring. The activated carbon ink was obtained from MeadWestvaco Corp of Stamford, Conn. under the name "DPX-8433-68B", and contained 14 wt. % activated carbon, 22 wt. % styrene acrylic binder, and 64 wt. % water. After stirring for 1.5 hours, the solution had a viscosity of 1,240 centipoise (Brookfield DV-I viscometer with LV-4 spindle at 60 RPM) and a solids content of 64%. The calculated concentration of each component of the aqueous formulation is set forth below in Table 12.

TABLE 12

Components of the Aqueous Formulation

| Component | Calculated Amount |
|---|---|
| Iron | 44.5% |
| Activated Carbon | 7.3% |
| Binder | 11.5% |
| Sodium Chloride | 2.3% |
| Water | 34.4% |

One side of the fabric was coated with the formulation using a #60 single wound metering rod. After applying the aqueous formulation, the coated fabric was then dried in a forced air oven at 110° C. for 20 to 25 minutes. The concentration of the components of the exothermic coating was then calculated from the initial fabric weight (2.2 grams), the dry coated fabric weight (28.2 grams), and the composition of the aqueous formulation. The results are set forth below in Table 13.

TABLE 13

Components of the Exothermic Coating

| Component | Calculated Amount |
|---|---|
| Iron | 67.8% |
| Activated Carbon | 11.1% |
| Binder | 17.5% |
| Sodium Chloride | 3.6% |
| Solids Add-On Level | ~1182% |

To test the effectiveness of the coated fabric in providing warmth, four pieces of the coated fabric (3.5"×4") were provided that had a total weight of 17.13 grams. A five-layered structure was designed to activate the exothermic reaction. Specifically, the five-layered structure included two of the coated fabric pieces positioned on one side of an absorbent layer, and the other two coated fabric pieces positioned on the other side of the absorbent layer. The iron coating on each coated fabric faced away from the absorbent layer. The absorbent layer was formed from 75 wt. % wood pulp fluff, 15 wt. % superabsorbent, and 10 wt. % of "ESC 806" PE/PP bicomponent fibers (Fibervisions, Inc.). The absorbent layer had a basis weight of 120 grams per square meter and a density of 0.12 grams per cubic centimeter. The wood pulp fluff was obtained from Weyerhaeuser under the name "NB416." The superabsorbent was obtained from Degussa AG under the name "SXM 9394." Prior to forming the multi-layered structure, the absorbent layer was wetted by spraying a fine mist of water to each side in an amount of 4 parts water to 1 part fabric.

Figure 9:
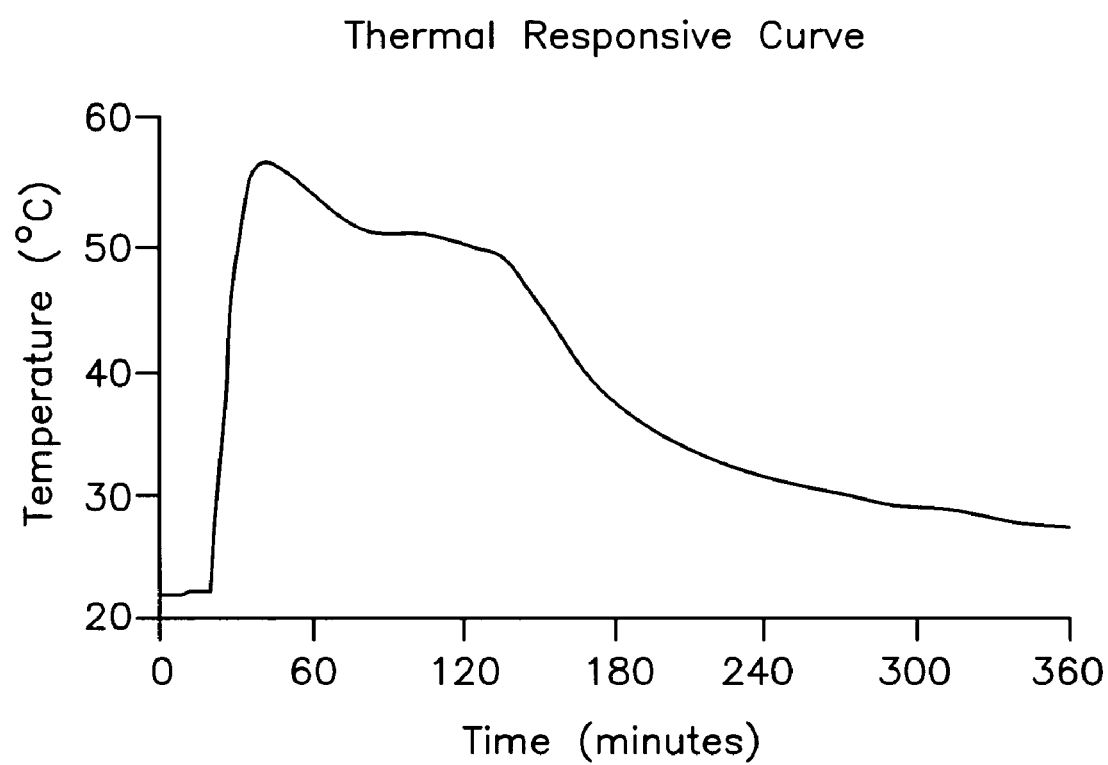
FIG. 9 is a thermal response curve showing temperature versus time for the sample of Example 7.

This five-layered structure was then placed inside of a rectangular pouch (4.5" by 4") made from three spunbond-film laminates (as described in Example 2) and an aluminum-coated SMS. The aluminum-coated SMS was used as the outside layer of the pouch, and all of the pouch layers were tacked together with an adhesive spray. The WVTR of the pouch was determined to be 293 grams/m$^2$/24 hrs. The pouch was then sealed and a thermocouple wired to a data collection device was attached to one side of the pouch. The temperature was recorded as a function of time (at 3-second intervals) to give the thermal curve shown in FIG. 9. As illustrated, the iron-coated fabric provided warmth (48° C. to 55° C.) for at least 2 hours.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A thermal covering that comprises an exothermic coating at a solids add-on level of from about 100% to about 5000%, the exothermic coating containing an oxidizable metal powder in an amount from about 40 wt. % to about 95 wt. %, a carbon component in an amount from about 0.01 wt. % to about 20 wt. %, a metal halide in an amount from about 0.01 wt. % to about 10 wt. %, and a binder in an amount from about 0.01 wt. % to about 20 wt. % within a single layer, wherein the binder comprises a polymer latex that is sufficiently crosslinked to be substantially insoluble in water and has a glass transition temperature of about 30° C. or less, wherein said exothermic coating is generally free of moisture prior to activation, and wherein exposure of said exothermic coating to oxygen and moisture activates an exothermic reaction to generate heat, such heat being transferable to a patient or user through an outer surface defined by the thermal covering.

2. The thermal covering of claim 1, wherein the solids add-on level of said exothermic coating is from about 400% to about 1200%.

3. The thermal covering of claim 1, wherein the solids add-on level of said exothermic coating is from about 200% to about 2400%.

4. The thermal covering of claim 1, wherein said metal is iron, zinc, aluminum, magnesium, or combinations thereof.

5. The thermal covering of claim 1, wherein said metal is in the form of a powder that constitutes from about 50 wt. % to about 90 wt. % of said exothermic coating.

6. The thermal covering of claim 1, wherein the thermal covering further comprises a breathable layer that is capable of regulating the amount of moisture and oxygen contacting said exothermic coating.

7. The thermal covering of claim 6, wherein said breathable layer comprises a breathable film.

8. The thermal covering of claim 7, wherein said breathable film is laminated to a nonwoven web.

9. The thermal covering of claim 6, wherein said breathable layer has a water vapor transmission rate of at least about 100 grams per square meter per 24 hours.

10. The thermal covering of claim 1, wherein the thermal covering further comprises an absorbent layer for absorbing and retaining moisture.

11. The thermal covering of claim 10, wherein said absorbent layer comprises cellulosic fibers.

12. The thermal covering of claim 11, wherein said absorbent layer further comprises a superabsorbent material.

13. The thermal covering of claim 1, further comprising a thermally conductive layer.

14. The thermal covering of claim 13, wherein said thermally conductive layer comprises a film, a fibrous material, or combinations thereof.

15. The thermal covering of claim 13, wherein said thermally conductive layer comprises a metallic coating.

16. The thermal covering of claim 13, wherein an additive is incorporated into said thermally conductive layer for enhancing thermal conductivity.

17. The thermal covering of claim 1, further comprising an insulation layer.

18. The thermal covering of claim 17, wherein said insulation layer comprises a nonwoven web.

19. The thermal covering of claim 1, wherein said outer surface is defined by a bodyside layer of the thermal covering.

20. The thermal covering of claim 19, further comprising an environment-side layer that defines a second outer surface of the thermal covering.

21. The thermal covering of claim 1, wherein the thermal covering comprises multiple substrates containing an exothermic coating.

22. The thermal covering of claim 1, further comprising a layer that contains moisture-retaining particles.

23. The thermal covering of claim 1, wherein said carbon component constitutes from about 0.1 wt. % to about 15 wt. % of said exothermic coating and said metal halide constitutes from about 0.5 wt. % to about 5 wt. % of said exothermic coating.

24. The thermal covering of claim 1, wherein said carbon component is activated carbon.

25. The thermal covering of claim 1, wherein said binder further comprises a nonionic cellulosic ether.

26. The thermal covering of claim 1, wherein said metal powder constitutes from about 50 wt. % to about 90 wt. % of said exothermic coating.

27. The thermal covering of claim 1, wherein said binder constitutes from about 0.1 wt. % to about 10 wt. % of said exothermic coating.

28. The thermal covering of claim 1, comprising:
   i) first and second substrates, each of which contains said exothermic coating;
   ii) first and second breathable layers for regulating the amount of moisture and oxygen contacting said exothermic coating; and
   iii) an absorbent layer for absorbing and retaining moisture, said absorbent layer being positioned between said first and second substrates, said first substrate being positioned between said absorbent layer and said first breathable layer, and said second substrate being positioned between said absorbent layer and said second breathable layer.

29. The thermal covering of claim 28, further comprising a thermally conductive layer, an insulation layer, or combinations thereof.

30. The thermal covering of claim 29, wherein said thermally conductive layer is located adjacent to said first breathable layer.

31. The thermal covering of claim 30, wherein said insulation layer is located adjacent to said second breathable layer.

32. The thermal covering of claim 31, further comprising a bodyside layer that is located adjacent to said thermally conductive layer.

33. The thermal covering of claim 32, further comprising an environment-side layer that is located adjacent to said insulation layer.

34. The thermal covering of claim 1, wherein the polymer latex has a glass transition temperature of from about −15° C. to about 15° C.

35. The thermal covering of claim 1, wherein the polymer latex includes a styrene-butadiene copolymer, polyvinyl acetate homopolymer, vinyl-acetate ethylene copolymer, vinyl-acetate acrylic copolymer, ethylene-vinyl chloride copolymer, ethylene-vinyl chloride-vinyl acetate terpolymer, acrylic polyvinyl chloride polymer, acrylic polymer, nitrile polymer, or a combination thereof.

* * * * *